US011965850B2

(12) United States Patent
Haick et al.

(10) Patent No.: US 11,965,850 B2
(45) Date of Patent: *Apr. 23, 2024

(54) BIOMIMETIC SENSING PLATFORM UNIT

(71) Applicant: TECHNION RESEARCH AND DEVELOPMENT FOUNDATION LIMITED, Haifa (IL)

(72) Inventors: Hossam Haick, Haifa (IL); Weiwei Wu, Zhejiang (CN)

(73) Assignee: TECHNION RESEARCH AND DEVELOPMENT FOUNDATION LIMITED, Haifa (IL)

( * ) Notice: Subject to any disclaimer, the term of this patent is extended or adjusted under 35 U.S.C. 154(b) by 85 days.

This patent is subject to a terminal disclaimer.

(21) Appl. No.: 17/540,359

(22) Filed: Dec. 2, 2021

(65) Prior Publication Data

US 2022/0091097 A1     Mar. 24, 2022

Related U.S. Application Data

(63) Continuation of application No. 16/486,583, filed as application No. PCT/IL2018/050193 on Feb. 21, 2018, now Pat. No. 11,209,418.

(30) Foreign Application Priority Data

Feb. 21, 2017    (IL) ........................................ 250695

(51) Int. Cl.
    *G01N 27/12*       (2006.01)
    *G01K 7/18*        (2006.01)
             (Continued)

(52) U.S. Cl.
    CPC ........... *G01N 27/125* (2013.01); *G01K 7/186* (2013.01); *G01L 19/0092* (2013.01); *G01N 33/497* (2013.01); *G01N 2033/4975* (2013.01)

(58) Field of Classification Search
    CPC ......... G01N 33/497; G01N 2033/4975; G01N 27/125; G01K 7/186; G01L 19/0092
    See application file for complete search history.

(56) References Cited

U.S. PATENT DOCUMENTS

| 4,021,414 A | 5/1977 | Saracsan |
| 8,366,630 B2 | 2/2013 | Haick |
| (Continued) | | |

FOREIGN PATENT DOCUMENTS

| CN | 109485824 A | 3/2019 |
| WO | 2005033685 A2 | 4/2005 |
| (Continued) | | |

OTHER PUBLICATIONS

Alvares et al., (2011) Nanoparticle films as biomimetic tactile sensors. Procedia Engineering 25: 1349-1352.

(Continued)

*Primary Examiner* — Benjamin R Schmitt
(74) *Attorney, Agent, or Firm* — Raphael Bellum PLLC

(57) ABSTRACT

The present invention provides a vapor-permeable flexible sensing platform unit comprising: a first porous membrane, wherein said membrane is substantially flexible and hydrophobic; and a volatile organic compounds (VOCs) sensor disposed on said membrane, the VOCs sensor comprising an electrode array and a conducting polymer porous film being in electric contact with said electrode array, wherein the VOCs sensor is insensitive to lateral strain. Further provided are a method of preparation of said platform unit and a lift-off, float-on (LOFO) method for the preparation of protonically doped polyaniline (PANI) thin films.

20 Claims, 17 Drawing Sheets

(51) Int. Cl.
*G01L 19/00* (2006.01)
*G01N 33/497* (2006.01)

(56) References Cited

U.S. PATENT DOCUMENTS

| | | | |
|---|---|---|---|
| 9,625,341 | B2 | 4/2017 | Haick |
| 2009/0111207 | A1* | 4/2009 | Choumane ......... G01N 21/6454 438/70 |
| 2012/0245434 | A1 | 9/2012 | Haick |
| 2012/0245854 | A1 | 9/2012 | Haick |
| 2013/0034910 | A1 | 2/2013 | Haick |
| 2013/0040399 | A1* | 2/2013 | BelBruno ............... H05K 3/10 436/149 |
| 2013/0041235 | A1 | 2/2013 | Rogers |
| 2015/0082920 | A1 | 3/2015 | Haick |
| 2015/0276372 | A1 | 10/2015 | Tata |
| 2016/0195488 | A1 | 7/2016 | Ensor |

FOREIGN PATENT DOCUMENTS

| | | | |
|---|---|---|---|
| WO | 2009066293 | A1 | 5/2009 |
| WO | 2009118739 | A1 | 10/2009 |
| WO | 2010079490 | A1 | 7/2010 |
| WO | 2011148371 | A1 | 12/2011 |
| WO | 2012023138 | A2 | 2/2012 |
| WO | 2013079469 | A1 | 6/2013 |
| WO | 2013144788 | A1 | 10/2013 |
| WO | 2013188675 | A1 | 12/2013 |
| WO | 2017029660 | A1 | 2/2017 |

OTHER PUBLICATIONS

An et al., (2015) Fabrication of planar and curved polyimide membranes with a pattern transfer method using ZnO nanowire arrays as templates. Materials Letters 149: 109-112.
Ayad and Zaki (2008) Quartz crystal microbalance and spectroscopy measurements for acid doping in polyaniline films. Science and Technology of Advanced Materials 9(1): 015007; 10 pages.
Broza and Haick (2013) Nanomaterial-based sensors for detection of disease by volatile organic compounds. Nanomedicine 8(5): 785-806.
Brust et al., (1994) Synthesis of thiol-derivatised gold nanoparticles in a two-phase liquid-liquid system. Journal of the Chemical Society, Chemical Communications (7): 801-802.
Fratoddi et al., (2015) Chemiresistive polyaniline-based gas sensors: A mini review. Sensors and Actuators B: Chemical 220: 534-548.
Haick et al., (2014) Assessment, origin, and implementation of breath volatile cancer markers. Chem Soc Rev 43(5): 1423-1449.
Hakim et al., (2012) Volatile organic compounds of lung cancer and possible biochemical pathways. Chem Rev 112(11): 5949-5966.
Hammock et al., (2013) 25th anniversary article: The evolution of electronic skin (e-skin): a brief history, design considerations, and recent progress. Adv Mater 25(42): 5997-6038.

Hong-Xing et al., (2010) Electrical resistance response of polyaniline films to water, ethanol, and nitric acid solution. Chinese Physics B 19(8): 088105; 6 pages.
Hostetler et al., (1998) Alkanethiolate gold cluster molecules with core diameters from 1.5 to 5.2 nm: core and monolayer properties as a function of core size. Langmuir 14(1): 17-30.
Huang et al., (2015) A High-Capacitance Salt-Free Dielectric for Self-Healable, Printable, and Flexible Organic Field Effect Transistors and Chemical Sensor. Advanced functional materials 25(24): 3745-3755.
Huynh and Haick (2016) Self-Healing, Fully Functional, and Multiparametric Flexible Sensing Platform. Advanced Materials 28(1): 138-143.
Huynh et al., (2016) Composites of Polymer and Carbon Nanostructures for Self-Healing Chemical Sensors. Advanced Materials Technologies 1(9): 1600187; 8 pages.
Kim and Kwak (2012) Flexible VOC sensors using conductive polymers and porous membranes for application to textiles. Fibers and Polymers 13(4): 471-474.
Li and Wan (1999) Stability of polyaniline synthesized by a doping-dedoping-redoping method. Journal of Applied Polymer Science 71(4): 615-621.
Li et al., (2008) Electrochemical fabrication of nanoporous polypyrrole thin films. Thin Solid Films 516(12): 3836-3840.
Mahadeva et al., (2011) Flexible humidity and temperature sensor based on cellulose-polypyrrole nanocomposite. Sensors and Actuators A: Physical 165(2): 194-199.
Segev-Bar and Haick (2013) Flexible Sensors Based on Nanoparticles. ACS Nano 7(10): 8366-8378.
Segev-Bar et al., (2015) High-Resolution Unpixelated Smart Patches with Antiparallel Thickness Gradients of Nanoparticles. Advanced Materials 27(10): 1779-1784.
Tee et al., (2012) An electrically and mechanically self-healing composite with pressure- and flexion-sensitive properties for electronic skin applications. Nature Nanotechnology 7: 825-832.
Wu et al., (2013) Surface Engineering Method to Fabricate a Bendable Self-Cleaning Surface with High Robustness. Science of Advanced Materials 5(8): 933-938.
Yamada et al., (2011) A stretchable carbon nanotube strain sensor for human-motion detection. Nat Nanotechnol 6(5): 296-301.
Yan et al., (2004) Preparation of porous polymer membranes using nano- or micro-pillar arrays as templates. Polymer 45(25): 8469-8474.
Yang et al., (2009) Power generation with laterally packaged piezoelectric fine wires. Nat Nanotechnol 4(1): 34-39.
Dai et al., (2015) Versatile method for the synthesis of porous nanostructured thin films of conducting polymers and their composites. RSC Adv 5: 34616-34621.
Anonymous: "Surface Properties", Feb. 2, 2023 (Feb. 2, 2023), pp. 1-3, XP093020453. Retrieved from the Internet: URL: https://polymerdatabase.com/polymer%20physics/SurfaceTension.html [retrieved on Feb. 2, 2023].

* cited by examiner

BIOMIMETIC SENSING PLATFORM UNIT

CROSS REFERENCE TO RELATED APPLICATIONS

This application is a Continuation Application of U.S. application Ser. No. 16/486,583, filed on Aug. 16, 2019, which is a National Phase Application of PCT International Application No. PCT/IL2018/050193, filed on Feb. 21, 2018, both of which are hereby incorporated by reference in their entirety.

FIELD OF THE INVENTION

The present invention is directed to a vapor-permeable flexible sensing platform unit comprising a porous membrane and a sensor of volatile organic compounds (VOCs) based on a conducting polymer porous film. The platform unit can further include a pressure and temperature sensor comprising a self-healing polymer and conductive nanostructures.

BACKGROUND OF THE INVENTION

Human skin can be seen as a layered stack structure containing three primary layers: the epidermis, the dermis and the hypodermis. Epidermis is the outer surface of human skin which serves as a protective barrier with the ability of keeping water in the body, preventing pathogens from entering and helping the skin regulate body temperature. Dermis is the layer of skin beneath the epidermis which comprises connective tissue and cushions the body from stress and strain. Dermis provides tensile strength and elasticity to the skin and harbors mechanoreceptors (nerve endings) that provide the sense of touch and heat. Between epidermis and dermis, there is a thin sheet of basement membrane which separates these two layers, repairs damaged skin and controls cell traffic and diffusion of bioactive molecules. Accordingly, the epidermis protects the skin, the basement membrane provides skin self-healing and the dermis senses touch and temperature.

In an attempt to mimic said numerous unique features of the human skin, various types of electronic devices, named electronic skins (E-skins), are being fabricated. The vast majority of currently available E-skins focus on strain (US Patent Application No. 2015/0276372), pressure (M. Segev-Bar, G. Konvalina, and H. Haick, Advanced Materials 27 (2015): 1779-1784), or temperature and humidity sensing (Mahadeva, Suresha K., Sungryul Yun, and Jaehwan Kim, Sensors and Actuators A: Physical 165 (2011) 194-199). Typically, the E-skin sensors are fabricated on a flexible substrate like Kapton, polydimethylsiloxane (PDMS) or a self-healing polymer (Yamada, Takeo, et al., Nature nanotechnology 6 (2011) 296-301). US Patent Application No. 2015/0082920 to some of the inventors of the present invention is directed to a modular platform unit comprising a plurality of sensors for the combined sensing of pressure, temperature and humidity, wherein the sensors are composed of a layer of metallic-capped nanoparticles casted on a flexible substrate or a rigid substrate and the platform unit can be used in artificial or electronic skin applications.

Products of metabolism in a form of volatile organic compounds (VOCs), which can be found in the human bodily fluids, including, inter alia, in the breath or skin secretion, are related to different specific biochemical pathways in the body. Analysis of VOCs can be performed by a non-invasive, fast, and cost effective technique involving the use of nanoscale sensors. WO 2009/066293, WO 2009/118739, WO 2010/079490, WO 2011/148371, WO 2012/023138, US 2012/0245434, US 2012/0245854, and US 2013/0034910 to some of the inventors of the present invention disclose apparatuses based on nanoparticle conducting cores capped with an organic coating for detecting volatile and non-volatile compounds, particularly for diagnosing various diseases and disorders. U.S. Pat. No. 8,366,630 to some of the inventors of the present invention is directed to sensors comprising single-walled carbon nanotubes (SWCNTs) coated with non-polar small organic molecules.

Conducting polymers represent an important class of organic materials with an enhanced resistivity towards external stimuli. Among them, polyaniline (PANI) has attracted wide interest because of the versatility in use, ease of synthesis, high yield and good environmental stability, together with a favorable response to guest molecules at room temperature (I. Fratoddi, I. Venditti, C. Cametti, and M. V. Russo, Sensors and Actuators B: Chemical, 220, 1 2015, 534-548). Moreover, PANI can be shaped into various structures with different morphologies, such as, but not limited to, thin films and nanofibers. PANI films can also be supported on different substrates, such as, for example, flexible and porous substrates (T. Kim and D. Kwak, Fibers and Polymers 2012, Vol. 13, No. 4, 471-474). Said features of PANI polymers have allowed a rapid development of ultrasensitive chemical sensors, which can be used, inter alia, for the VOCs sensing.

Integration of VOCs, pressure and temperature sensors on a single platform would provide a smart E-skin which does not only sense the stimulation from the environment but also monitors the health condition of human beings. However, despite extensive development in the field of electronic skin, said multifunctioning still remains a challenge. A non-biological and flexible self-healing platform with tailored sensitivity toward one of or a combination of pressure, strain, gas analytes, and temperature has been described (Huynh, Tan-Phat, and Hossam Haick, Advanced Materials 28 (2016): 138-143).

A possibility of monitoring the health condition of a subject in real-time by sensing VOCs secreted by human skin is of a particular interest, for example, in the robotic prosthetics industry. The main hindrance to using the currently existing E-skins for sensing VOCs emitted from human skin is that said E-skins are generally not permeable to vapors. The VOCs will thus accumulate in the headspace between E-skin and real skin, which is harmful to the VOCs sensor. To the inventors' best knowledge, no permeable E-skins have been reported up to date. Additionally, response of thin film-based flexible sensors can be affected by mechanical changes, such as deformation or bending, which is undesirable in electronic skin applications. Fabricating thin sensing films which can be used in flexible sensors to provide a stable performance under lateral strain and eliminating the effect of contact resistance caused by carrier scattering between nanomaterials' interface still remains a great challenge.

There still exists an unmet need for multi-purpose sensing devices, which are permeable to VOCs and are unaffected by lateral strain, for use in electronic skin and/or chemical sensing applications.

SUMMARY OF THE INVENTION

The present invention provides a vapor-permeable flexible sensing platform unit comprising a sensor of volatile organic compounds (VOCs), termed herein "VOCs sensor", comprising a porous film of conducting polymer supported on a porous flexible membrane. Owing to the vapor-permeable structure, said platform unit can beneficially be used for sensing VOCs emitted or excreted from human skin. The present invention is based in part on the unexpected finding that the VOCs sensor based on the conducting polymer porous film, while being able to detect VOCs, is insensitive to lateral strain, thereby allowing integration of the platform unit on non-rigid surfaces, such as human, electronic or artificial skin. The inventors have surprisingly found that thin films comprising conducting polymer polyaniline (PANI), which is protonically doped, shows no obvious response when lateral strain is applied thereto. Said PANI films were found to provide quantitative response to different VOCs, which are highly correlative with exhaled VOCs both from the respiratory tract and skin and which have been considered as biomarkers for disease diagnose and health monitoring. The inventors have further developed an eco-friendly method of preparation of said films, which can be produced in a form of continuous, porous or free-standing films. Porous conducting polymer films were used to fabricate a vapor-permeable flexible sensing platform unit of the present invention.

The VOCs sensor is supported on a porous membrane, which allows vapor transport to and from the sensor. Additionally, said membrane is hydrophobic, thereby eliminating the effect of perspiration on the sensor, and substantially flexible, such that the platform unit can be used on non-rigid surfaces, e.g., being attached to skin.

In some embodiments, the platform unit further includes a pressure and temperature sensor, thereby offering additional sensing abilities. The pressure and temperature sensor can be based on a combination of conductive nanostructures and a self-healing polymer, which imparts self-healing properties to the sensing platform unit as a whole. In order to further mimic the beneficial properties of human skin, the platform unit of the present invention can include additional membranes, for example, protecting the device from contamination and/or having a self-cleaning ability.

Thus, according to a first aspect, the present invention provides a vapor-permeable flexible sensing platform unit comprising: a first porous membrane, wherein said membrane is substantially flexible and hydrophobic; and a VOCs sensor disposed on said membrane, the VOCs sensor comprising an electrode array and a conducting polymer porous film being in electric contact with said electrode array, wherein the VOCs sensor is insensitive to lateral strain.

The conducting polymer can be selected from the group consisting of polyaniline (PANI), polythiophene, poly(3,4-ethylenedioxythiophene)-poly(styrene-sulfonate) (PEDOT:PSS), polypyrrole, polydiketopyrrolopyrrole, and derivatives and combinations thereof. Each possibility represents a separate embodiment of the invention. In some exemplary embodiments, the polymer is PANI. In further embodiments, PANI is protonically doped with a dopant. The dopant can be selected from the group consisting of hydrochloric acid, sodium bisulfate, salicylic acid, maleic acid, fumaric acid, benzoic acid, phosphoric acid and any combination thereof. Each possibility represents a separate embodiment of the invention.

In some embodiments, the conducting polymer porous film has at least one non-uniform surface. In further embodiments, said non-uniform surface comprises wrinkles. In further embodiments, the surface coverage of the non-uniform surface by the wrinkles ranges from about 1% to about 10%.

In some embodiments the conducting polymer porous film has a vertically ordered porous structure. In some embodiments, the conducting polymer porous film has a mean pore size ranging from about 20 nm to about 500 nm. In additional embodiments, the conducting polymer porous film has a porosity ranging from about 30% to about 80% of the total film volume.

In some embodiments, the conducting polymer porous film has a thickness ranging from about 50 nm to about 300 nm.

In some embodiments, the electrode array comprises electrodes made of a metal selected from Au, Ti, Cu, Ag, Pd, Pt, Ni, Al, and combinations thereof. Each possibility represents a separate embodiment of the invention. In certain embodiments, the electrode array comprises interdigitated electrodes.

In some embodiments, the platform unit further comprises a pressure and temperature sensor. In further embodiments, the pressure and temperature sensor comprises a self-healing porous film, comprising a self-healing polymer and conductive nanostructures selected from the group consisting of metallic nanoparticles capped with an organic coating, carbon-based nanostructures and combinations thereof. Each possibility represents a separate embodiment of the invention.

The metal nanoparticles can be selected from the group consisting of Au, Ag, Ni, Co, Pt, Pd, Cu, Al, Zn, Fe, and combinations thereof. In further embodiments, metal nanoparticles comprise metal alloys selected from the group consisting of Au/Ag, Au/Cu, Au/Ag/Cu, Au/Pt, Au/Pd, Au/Ag/Cu/Pd, Pt/Rh, Ni/Co, and Pt/Ni/Fe. Each possibility represents a separate embodiment of the invention.

The organic coating of the metal nanoparticles can comprise compounds selected from the group consisting of alkylthiols, arylthiols, alkylarylthiols, alkylthiolates, and combinations thereof. Each possibility represents a separate embodiment of the invention.

The carbon-based nanostructures can be selected from unordered nanostructures (0D), one-dimensional nanostructures (1D), two-dimensional nanostructures (2D) nanostructures and combinations thereof. In certain embodiments, the carbon-based nanostructures are selected from the group consisting of carbon powder, carbon nanotubes, graphite, and combinations thereof. Each possibility represents a separate embodiment of the invention.

The self-healing polymer can comprise polymeric chains dynamically crosslinked by covalent disulfide bonds or by hydrogen bonds. In some embodiments, the self-healing polymer is selected from the group consisting of poly(propylene-urethaneureaphenyl-disulfide), poly(urethane-carboxyphenyl-disulfide), and poly(2-hydroxypropyl methacrylate)/poly(ethyleneimine). Each possibility represents a separate embodiment of the invention. In certain embodiments the self-healing polymer comprises poly(propylene-urethaneureaphenyl-disulfide).

In certain embodiments, the nanostructures are dispersed in the self-healing polymer. In further embodiments, the self-healing porous film has conductivity ranging from about $0.0000001\ S*cm^{-1}$ to about $1\ S*cm^{-1}$. In some embodiments, the self-healing porous film comprises nanofibers. In further embodiments, the self-healing porous film is made of polymer nanofibers. In some embodiments, the self-healing porous film has a mean pore size ranging from about 100 nm to about 5 μm. In additional embodiments, the self-healing porous film has a porosity ranging from about 30% to about 80% of the total film volume.

According to some embodiments, the pressure and temperature sensor further comprises an electrode array. In certain such embodiments, the self-healing porous film is in electric contact with said electrode array. In some embodiments, the electrode array comprises electrodes made of a metal selected from Au, Ti, Cu, Ag, Pd, Pt, Ni, Al, and combinations thereof. Each possibility represents a separate embodiment of the invention. In certain embodiments, the electrode array comprises interdigitated electrodes. In some embodiments, the electrode array is the same as the electrode array of the VOCs sensor.

The VOCs sensor, the pressure and temperature sensor or both can be configured in a form of a resistive sensor.

According to some embodiments, the platform unit further comprises a second porous membrane disposed between the VOCs sensor and the pressure and temperature sensor. In particular embodiments, said membrane is electrically insulating.

According to some embodiments, the platform unit further comprises a third porous membrane, substantially covering the pressure and temperature sensor, In certain embodiments, the third porous membrane is hydrophobic. In additional embodiments, the third porous membrane is self-cleaning.

In some embodiments, the first porous membrane, the second porous membrane and/or the third porous membrane comprise a polymer selected from the group consisting of a fluoropolymer, aromatic polymer, polyamide, aramide and combinations, and derivatives thereof. In further embodiments, the first porous membrane, the second porous membrane and/or the third porous membrane comprise a polymer selected from the group consisting of polyvinylidene difluoride, (PVDF), Poly(vinylidene fluoride-co-hexafluoropropylene) (PVDF-HFP), polystyrene (PS), Poly(styrene-butadiene-styrene) (SBS), Nylon and combinations thereof. Each possibility represents a separate embodiment of the invention.

In some embodiments, at least one of the first porous membrane, the second porous membrane and the third porous membrane has a mean pore size ranging from about 20 nm to about 20 µm. In additional embodiments, at least one of the first porous membrane, the second porous membrane and the third porous membrane has a porosity ranging from about 30% to about 90% of the total membrane volume. In some embodiments, at least one of the first porous membrane, the second porous membrane and the third porous membrane has a thickness ranging from about 200 nm to about 5 µm. In some embodiments, at least one of the first porous membrane, the second porous membrane and the third porous membrane comprises nanofibers.

In some embodiments, the platform unit according to the principles of the invention has a thickness below about 500 µm.

In some embodiments, the platform unit according to the principles of the invention is integrated on electronic or artificial skin surface.

According to some embodiments, the platform unit is for use in monitoring health of a subject, comprising detecting VOCs emitted or excreted from skin of the subject by the VOCs sensor. In further embodiments, the platform unit is for use in monitoring health of a subject, comprising detecting VOCs emitted from breath of the subject by the VOCs sensor. The platform unit can be placed on a skin surface of a subject, wherein the first porous membrane contacts the skin surface.

The platform unit can be coupled with a detection device for measuring a change in at least one property of at least one of the VOCs sensor and the pressure and temperature sensor. The at least one property of at least one of the VOCs sensor and the pressure and temperature sensor can be selected from the group consisting of resistance, conductance, direct current (DC), alternating current (AC), capacitance, impedance, electrical potential, and voltage threshold. Each possibility represents a separate embodiment of the invention.

In some embodiments, the platform unit is coupled with a computing system configured for executing various algorithms stored on a non-transitory memory, the algorithms being selected from the group consisting of artificial neural network (ANN) algorithm, support vector machine (SVM), discriminant function analysis (DFA), principal component analysis (PCA), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, nearest neighbor, Fisher linear discriminant analysis (FLDA), soft independent modeling of class analogy (SIMCA), K-nearest neighbors (KNN), genetic algorithms, and fuzzy logic algorithms and canonical discriminant analysis (CDA). Each possibility represents a separate embodiment of the invention.

According to another aspect, there is provided a method for fabricating the vapor-permeable flexible sensing platform unit according to the principles of the invention, the method comprising: providing a first porous membrane, which is substantially flexible and hydrophobic; forming an electrode array; providing a conducting polymer porous film; and disposing said film on the electrode array or the first porous membrane, wherein the film is in electric contact with the electrode array, thereby forming the VOCs sensor.

According to some embodiments, the electrode array is formed on the first porous membrane and the conducting polymer porous film is disposed on said electrode array. According to some embodiments, the electrode array is formed on the first porous membrane and the conducting polymer porous film is disposed adjacently to said electrode array. According to some embodiments, the conducting polymer porous film is disposed on the first porous membrane and the electrode array is formed on said conducting polymer porous film.

According to some embodiments, the step of providing a conducting polymer porous film comprises applying a solution of a conducting polymer onto a substrate having a non-uniform surface. The step of applying a solution of a conducting polymer onto a substrate having a non-uniform surface can be performed by a process selected from the group consisting of spin-coating, dip-coating, drop-coating, and screen printing. Each possibility represents a separate embodiment of the invention. In certain embodiments, said process is spin-coating.

In some embodiments, the substrate comprises a sacrificial pattern. In certain embodiments, the pattern has a vertically ordered structure. In some embodiments, the substrate is a rigid substrate. In other embodiments, the substrate comprises a rigid base. The sacrificial pattern can be formed on said rigid base.

In particular embodiments, the substrate is made of an inorganic material. The inorganic material can be selected from the group consisting of glass, silicon wafer, sapphire, quartz, metal oxide, and combinations thereof. The substrate can comprise a combination of inorganic materials.

In certain embodiments, the substrate comprises nanostructures epitaxially grown thereon. The nanostructures can be selected from the group consisting of nanowires, nanorods, nanotubes, nanoneedles and combinations thereof. In some embodiments, the nanostructures comprise a material selected from the group consisting of ZnO, $Co_3O_4$, NiO, $Fe_2O_3$, and combinations thereof. In further embodiments, the epitaxial growth method comprises depositing a seed layer of nanoparticles comprising the same material as the nanostructures on the substrate. The seed layer can be deposited by a process selected from the group consisting of magnetron sputtering, drop-casting, electron beam deposition, sol-gel method and combinations thereof. In still further embodiments, the epitaxial growth method comprises aqueous immersion method, chemical vapor deposition, physical vapor deposition, hydrothermal method, solvent thermal method, electrochemical deposition, and combinations thereof. Each possibility represents a separate embodiment of the invention.

In some exemplary embodiments, the substrate comprises epitaxially grown ZnO nanowires. In further embodiments, said ZnO nanowires are grown on a glass substrate.

In some embodiments, the step of providing a conducting polymer porous film comprises removing the sacrificial pattern from the substrate, while the conducting film remains on the substrate. In further embodiments said step comprises removing the nanostructures from the substrate by a process selected from acid dissolution and etching.

In some embodiments, the conducting polymer is selected from the group consisting of polyaniline (PANI), polythiophene, poly(3,4-ethylenedioxythiophene)-poly(styrenesulfonate) (PEDOT:PSS), polypyrrole, polydiketopyrrolopyrrole, and derivatives and combinations thereof. Each possibility represents a separate embodiment of the invention.

According to some embodiments, the conducting polymer is PANI. In certain such embodiments, the substrate is a substantially rigid inorganic substrate. The substrate can comprise ZnO nanowires. The rigid portion of the substrate can be made of glass. In further embodiments, the step of providing a conducting polymer porous film further comprises protonically doping the PANI film and/or removing the ZnO nanowires. In certain embodiments, doping the PANI film and/or removing the ZnO nanowires comprises immersing the PANI film supported on the substrate into an acidic solution. In further embodiments, the step of providing a conducting polymer porous film comprises contacting the doped PANI film supported on the substrate with a portion of deionized water, thereby separating the doped PANI film from the substrate. In still further embodiments, the step of providing a conducting polymer porous film comprises dedoping the PANI film by replacing the portion of water, being in contact with the PANI film with an additional portion of deionized water. In certain embodiments, the water replacement procedure is repeated at least three times. In further embodiments, the step of providing a conducting polymer porous film comprises protonically doping the dedoped PANI film. In still further embodiments, the protonical doping comprises contacting the PANI film with an acidic solution. The acidic solution can comprise an acid selected from the group consisting of hydrochloric acid, sodium bisulfate, salicylic acid, maleic acid, fumaric acid, benzoic acid, phosphoric acid and any combination thereof. Each possibility represents a separate embodiment of the invention. The concentration of said acidic solution can range from about 0.01M to about 10M.

According to some embodiments, the step of forming an electrode array comprises depositing a metal on the first porous membrane or the conducting polymer porous film by a method selected from the group consisting of e-beam evaporation, physical vapor deposition, sputter-deposition, drop-casting, field enhanced deposition, soft lithography, inkjet printing, screen printing and combinations thereof. The metal can be selected from the group consisting of Au, Ti, Cu, Ag, Pd, Pt, Ni, Al, and combinations thereof. Each possibility represents a separate embodiment of the invention. In certain embodiments, the step of forming an electrode array comprises applying a shadow mask during the metal deposition.

According to some embodiments, the step of providing a first porous membrane comprises preparing a solution of a polymer powder and electrospinning said solution, wherein electrospinning comprises using at least one spinneret connected to a power source and a collecting drum. The spinneret can be further connected to a pump. The polymer powder can include a polymer selected from the group consisting of polyvinylidene difluoride, (PVDF), Poly(vinylidene fluoride-co-hexafluoropropylene) (PVDF-HFP), polystyrene (PS), Poly(styrene-butadiene-styrene) (SBS), Nylon and combinations thereof. Each possibility represents a separate embodiment of the invention. In some embodiments, the weight ratio of the polymer in the solution ranges from about 10% (w/w) to about 40% (w/w).

The method according to the principles of the present invention can further comprise a step of forming a second porous membrane on the conducting polymer porous film. The second porous membrane can be formed by applying a solution of a polymer powder onto said film. The polymer can be selected from the group consisting of polyvinylidene difluoride, (PVDF), Poly(vinylidene fluoride-co-hexafluoropropylene) (PVDF-HFP), polystyrene (PS), Poly(styrene-butadiene-styrene) (SBS), Nylon and combinations thereof. Each possibility represents a separate embodiment of the invention. In some embodiments, the weight ratio of the polymer in the solution ranges from about 10% (w/w) to about 40% (w/w).

In some embodiments, the at least one spinneret comprises a nozzle having an inner diameter ranging from about 100 μm to about 900 μm. In some embodiments, electrospinning is performed by feeding the solution to the spinneret at a feeding rate ranging from about 0.1 ml/hour to about 15 ml/hour. In some embodiments, the voltage applied to the spinneret by the power source ranges from about 8 Volt to about 60 Volt. In some embodiments, the distance between the nozzle and the collecting drum ranges from about 5 cm to about 40 cm.

In some embodiments, the method of the present invention further comprises a step of forming a self-healing film comprising mixing a self-healing polymer and conductive nanostructures selected from the group consisting of metallic nanoparticles capped with an organic coating, carbon-based nanostructures, and combinations thereof. In further embodiments, the method comprises applying said mixture onto the second porous membrane, thereby forming a pressure and temperature sensor. In some embodiments, the method comprises dispersing the conductive nanostructures in an organic solvent under sonication. In further embodiments, the method comprises adding the self-healing polymer to the formed dispersion under sonication.

In some embodiments, the pressure and temperature sensor further comprises an electrode array. In certain such embodiments, the method comprises forming an electrode array on the self-healing film or on the second porous membrane, such that the self-healing film is in electric contact with the electrode array. In certain embodiments, the method comprises applying the mixture of the self-healing polymer and conductive nanostructures onto the electrode array.

The step of forming the electrode array can include depositing a metal on a substrate by a method selected from the group consisting of e-beam evaporation, physical vapor deposition, sputter-deposition, drop-casting, field enhanced deposition, soft lithography, inkjet printing, screen printing and combinations thereof. The metal can be selected from the group consisting of Au, Ti, Cu, Ag, Pd, Pt, Ni, Al, and combinations thereof. Each possibility represents a separate embodiment of the invention. In certain embodiments, the step of forming an electrode array on the substrate comprises applying a shadow mask during the metal deposition. The substrate can be selected from a second porous membrane and a self-healing film.

In further embodiments, the method comprises forming a third porous membrane substantially covering the pressure and temperature sensor. The third membrane can be formed by applying a solution of a polymer powder onto the self-healing film. The polymer can be selected from the group consisting of polyvinylidene difluoride, (PVDF), Poly (vinylidene fluoride-co-hexafluoropropylene) (PVDF-HFP), polystyrene (PS), Poly(styrene-butadiene-styrene) (SBS), Nylon and combinations thereof. Each possibility represents a separate embodiment of the invention. In some embodiments, the weight ratio of the polymer in the solution ranges from about 10% (w/w) to about 40% (w/w).

In one embodiment, the step of applying a solution of a polymer powder comprises electrospinning said solution, wherein electrospinning comprises using at least one spinneret connected to a power source, and a collecting drum. In one embodiment the step of applying a mixture of a self-healing polymer and conductive nanostructures comprises electrospinning said mixture, wherein electrospinning comprises using at least one spinneret connected to a power source, and a collecting drum. The spinneret can be further connected to a pump.

In some embodiments, the at least one spinneret comprises a nozzle having an inner diameter ranging from about 100 μm to about 900 μm. In some embodiments, electrospinning is performed by feeding the solution to the spinneret at a feeding rate ranging from about 0.1 ml/hour to about 15 ml/hour. In some embodiments, the voltage applied to the spinneret by the power source ranges from about 8 Volt to about 60 Volt. In some embodiments, the distance between the nozzle and the collecting drum ranges from about 5 cm to about 40 cm.

In certain embodiments, each one of the first porous membrane, second porous membrane, pressure and temperature sensor, and third porous membrane are formed by electrospinning, the process comprising placing the first porous membrane and the VOCs sensor on the collecting drum and sequentially electrospinning the respective polymer powder solutions and the mixture of the self-healing polymer and conductive nanostructures onto the top layer of the platform unit.

In yet another aspect there is provided a lift-off, float-on (LOFO) method for the preparation of a protonically doped polyaniline (PANI) thin film, the method comprising the following consecutive steps: (a) applying PANI organic solution onto a rigid inorganic substrate, thereby obtaining a PANI film supported on said substrate; (b) protonically doping the obtained PANI film; (c) contacting the doped PANI film supported on the substrate with a portion of deionized water, thereby separating the doped PANI film from the substrate; (d) dedoping the PANI film by replacing the portion of water, being in contact with the PANI layer with an additional portion of deionized water; and (e) protonically doping the dedoped PANI film.

In some embodiments, the LOFO method of the present invention is characterized by that it does not include the use of an organic solvent. In further embodiments, the LOFO method does not include the use of an etching solution.

In some embodiments, the inorganic substrate has a water contact angle of less than about 10°. In some embodiments, the PANI organic solution comprises N-methyl-2-pyrrolidone (NMP) as a solvent. In certain such embodiments, the inorganic substrate has a contact angle with NMP of less than about 15°.

In some embodiments, the LOFO method comprises enhancing the wettability of the rigid inorganic substrate by using a process selected from the group consisting of plasma treatment, strong oxidant liquid treatment, and a combination thereof.

The rigid inorganic substrate can be made of a material selected from the group consisting of glass, silicon wafer, sapphire, quartz, and combinations thereof. The inorganic substrate can have a substantially smooth surface or a non-uniform surface. The substrate having a non-uniform surface can be used for the preparation of a porous PANI film.

In certain embodiments, the concentration of PANI in the organic solution ranges from about 0.01 g/ml to about 0.2 g/ml.

The step of applying PANI organic solution to the rigid inorganic substrate in step (a) can comprise a method selected from the group consisting of spin-coating, dip-coating, drop-coating, and screen printing. Each possibility represents a separate embodiment of the invention. In certain embodiments, said process is spin-coating.

In some embodiments, the spin-coating is performed at a rotating speed ranging from 500 rpm to about 5000 rpm. In further embodiments, the spin-coating is performed for a time period ranging from about 30 seconds to about 20 minutes.

In some embodiments, protonicaly doping the PANI film in step (b) comprises contacting the PANI film with an acid in a form selected from acid vapor and/or acidic solution. Protonically doping the PANI film in step (e) can comprise contacting the PANI film with an acidic solution. Said contacting can include immersing in water or placing on the water surface. The acid can be selected from the group consisting of hydrochloric acid, sodium bisulfate, salicylic acid, maleic acid, fumaric acid, benzoic acid, phosphoric acid and any combination thereof. Each possibility represents a separate embodiment of the invention. In some embodiments, the concentration of the acidic solution ranges from about 0.01M to about 10M.

According to some embodiments, the LOFO method includes replacing the portion of water in step (d) for at least three times. In further embodiments, the water is replaced for at least three times in 48 hours.

In some embodiments, the LOFO method further comprises a step of transferring the doped PANI film to a final substrate. The final substrate can be selected from the group consisting of a rigid substrate, flexible substrate, continuous substrate, porous substrate, and hollow substrate. Each possibility represents a separate embodiment of the invention. The rigid final substrate can have a substantially flat or a curved surface. The hollow substrate can be used to prepare a substantially self-standing PANI film. In some embodiments, the hollow substrate comprises a frame.

In some embodiments, the LOFO method comprises a step of drying the doped PANI film supported on the final substrate in a vacuum chamber at a pressure of below about 10000 Pa. The method can further include increasing the pressure in the vacuum chamber to about 1 Atm or higher.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
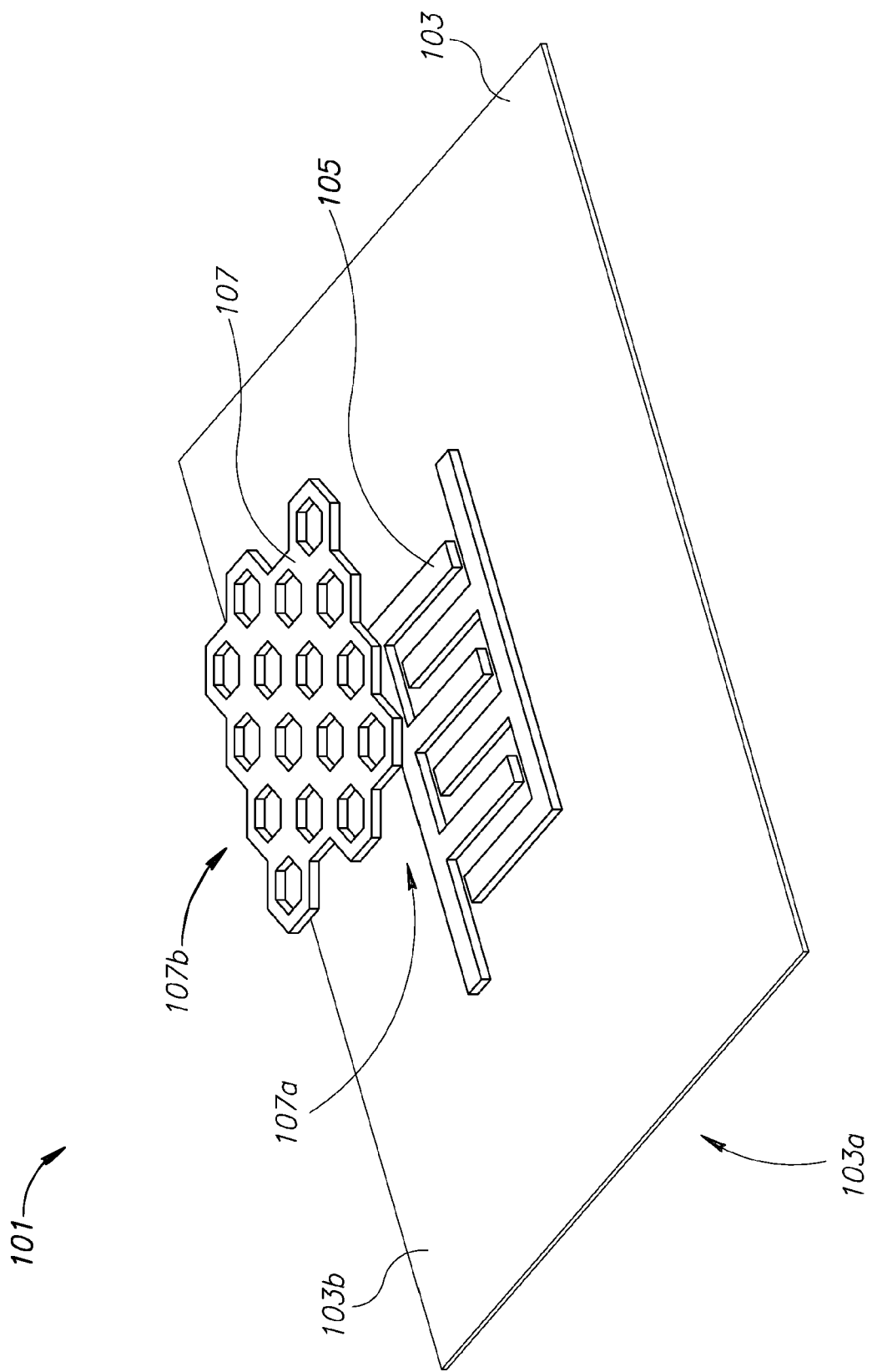
FIG. 1: A schematic exploded view of the vapor-permeable flexible sensing platform unit comprising a first porous membrane and a VOCs sensor, according to some embodiments of the invention.

The present invention provides a modular matrix or platform unit for the detection of volatile organic compounds and the method of preparation of said platform unit. Each component of the platform unit is porous and vapor-permeable, thereby preventing damaging accumulation of the VOCs inside said unit. In particular, provided herein is a vapor-permeable, flexible sensing platform unit comprising a VOCs sensor comprising a porous film of a conducting polymer and an electrode array, which are supported on a porous hydrophobic membrane. It was unexpectedly found by the inventors of the present invention that the porous VOCs sensor can detect VOCs under varying lateral strain, wherein the response of the sensor is not affected by strain. The combination of the vapor permeability and strain insensitivity of the platform unit makes it particularly suitable for use in artificial and electronic skin applications, robotics, prosthetics and human health monitoring through the VOCs analysis.

The inventors have further developed an eco-friendly method of preparation of the conducting polymer films, which does not require the use of organic solvents or strong chemical etching solutions for obtaining free-standing films or films supported on organic or polymeric surfaces.

It has been further surprisingly discovered by the inventors that said conductive films can also detect pressure and temperature, while the response of the conductive film-based sensors to environmental parameters and VOCs could be decoupled. Accordingly, the VOCs sensor can be used to detect pressure and/or temperature in addition to the VOCs sensing. Alternatively, the platform unit can include a different type of the sensor for the detection of pressure and/or temperature.

The present invention therefore provides a flexible platform unit based on a conducting polymer porous film with excellent sensitivity to volatile analytes, which is not affected by accumulation of the VOCs or by lateral strain.

The platform unit can further include a self-healing pressure and temperature sensor and additional functional layers, thereby providing multiple sensing abilities and various beneficial features mimicking human skin, such as self-healing, self-cleaning and protection against contamination.

Thus, according to some aspects and embodiments, the present invention provides a vapor-permeable flexible sensing platform unit comprising: a first porous membrane, wherein said membrane is substantially flexible and hydrophobic; and a volatile organic compounds (VOCs) sensor disposed on said membrane, the VOCs sensor comprising an electrode array and a conducting polymer porous film being in electric contact with said electrode array, wherein the VOCs sensor is insensitive to lateral strain.

The term "insensitive", as used herein, refers in some embodiments to a response of a sensor to a stimulus, which is not higher than 2% of the baseline signal of the sensor. The term "baseline", as used herein, refers in some embodiments to a signal of a sensor in the absence of said stimulus and other stimuli. In further embodiments, the term "baseline" refers to a signal of a sensor which is exposed to defined temperature and/or pressure conditions. In certain embodiments, the term "insensitive" refers to a response of a sensor to a stimulus, which is not higher than 1% of the baseline signal of the sensor. In further embodiments, the term "insensitive" refers to a response of a sensor to a stimulus, which is not higher than 0.5% of the baseline signal of the sensor.

According to some embodiments, the platform unit includes multiple layers. In some embodiments, the platform unit includes at least two layers. In further embodiments, the platform unit includes at least three layers, at least four layers or at least five layers. Each possibility represents a separate embodiment of the invention.

FIG. 1 schematically represents an exploded view of platform unit 101, according to some embodiments of the invention. Platform unit 101 includes first porous membrane 103, electrode array 105 and conducting polymer porous film 107. Electrode array 105 is disposed on first porous membrane 103 and conducting polymer porous film 107 is disposed on electrode array 105, being in electrical contact therewith. Combination of electrode array 105 and conducting polymer porous film 107 forms a VOCs sensor.

According to some embodiments, the electrode array and the conducting polymer porous film are disposed on the first porous membrane.

First porous membrane 103 has bottom surface 103a and top surface 103b. Top surface 103b is in contact with electrode array 105. Top surface 103b can further be in contact with conducting polymer porous film 107. Bottom surface 103a is configured to contact artificial skin surface, electronic skin surface or human skin surface (not shown).

Conducting polymer porous film 107 has bottom surface 107a and top surface 107b. Bottom surface 107a can be in contact with first porous membrane 103 and/or electrode array 105. Top surface 107b can be in contact with a second porous membrane or a pressure or temperature sensor (not shown). Top surface 107b can further be in contact with an electrode array of the VOCs sensor (not shown).

According to some embodiments, the electrode array is formed on the first porous membrane and the conducting polymer porous film is disposed adjacently to said electrode array. According to some embodiments, the conducting polymer porous film is disposed on the first porous membrane and the electrode array is formed on said conducting polymer porous film.

First Porous Membrane

The first porous membrane acts as a substrate of the sensing platform unit. The first porous membrane can be made of any suitable polymeric material, which can be formed into a porous and substantially flexible film. The term "substantially flexible", as used herein and in various embodiments, refers to a membrane which is configured to elastically deform in response to pressure, wherein said deformation is proportional to the amount of applied pressure. In some embodiments, the first porous membrane is configured to separate the sensing platform unit from the surface to which it is attached, for example, from human's skin. Accordingly, it is desirable that the first porous membrane protects the platform unit, and in particular, the VOCs sensor, from perspiration. In certain such embodiments, the first porous layer is hydrophobic.

The term "hydrophobic", as used herein, refers in some embodiments to an object and/or a material, having a water contact angle above about 90°. In further embodiments, the term "hydrophobic" refers to an object and/or a material, having a water contact angle above about 100°, above about 110° or above about 120°. Each possibility represents a separate embodiment of the invention.

The first porous membrane can include a polymer selected from a fluoropolymer, aromatic polymer, polyamide, aramide and combinations thereof. Non-limiting examples of polymers suitable for use in the first membrane of the platform unit include polyvinylidene difluoride (PVDF), Poly(vinylidene fluoride-co-hexafluoropropylene) (PVDF-HFP), polystyrene (PS), Nylon and combinations thereof. In some exemplary embodiments, the first membrane is made of PVDF. In additional exemplary embodiments, the first membrane is made of PVDF-HFP. In further exemplary embodiments, the first membrane is made of PS. In yet further exemplary embodiments, the first membrane is made of Nylon.

The first membrane is characterized by high porosity. In some embodiments, the first porous membrane has a mean pore size ranging from about 20 nm to about 20 μm. In further embodiments, the first porous membrane has a mean pore size ranging from about 50 nm to about 10 μm, from about 100 nm to about 5 μm, from about 200 nm to about 2 μm or from about 500 nm to about 1 μm. In certain embodiments, the first porous membrane has a mean pore size of at least about 50 nm, at least about 75 nm or at least about 100 nm. Each possibility represents a separate embodiment of the invention.

In some embodiments, the first porous membrane has a porosity ranging from about 30% to about 90% of the total membrane volume. In further embodiments, the first porous membrane has a porosity ranging from about 40% to about 80%, or from about 50% to about 70%, of the total membrane volume. In certain embodiments, the first porous membrane has a porosity of at least about 40%, at least about 50% or at least about 60% of the total membrane volume. Each possibility represents a separate embodiment of the invention.

According to some embodiments, the first porous membrane comprises polymer nanofibers. The mean thickness of a nanofiber of the first porous membrane can range from about 200 nm to about 5 μm. In certain embodiments, the mean thickness of a nanofiber of the first porous membrane ranges from about 500 nm to about 2 μm. According to further embodiments, the first porous membrane is prepared by electrospinning.

The thickness of the first porous membrane is preferably relatively low, in order to keep the total thickness of the platform unit low. In some embodiments, the first porous membrane has a thickness ranging from about 200 nm to about 5 µm. In further embodiments, the first porous membrane has a thickness ranging from about 500 nm to about 2 µm.

The first porous membrane can have any desirable geometry. In rectangular geometries, the length and/or width of the first porous membrane can range between about 0.01-10 cm.

Electrode Array

The vapor-permeable sensing platform unit comprises an electrode array which is in electric contact with the conducting polymer porous film. In some embodiments, the conducting polymer porous film generates an electric signal upon detecting one or more VOCs. The electrode array, which is coupled to the conducting film, enables the measurement and transmittance of the electric signals generated by the film. Said electric signal can include, inter alia, changes in resistance or conductance of the film.

The electrode array can be further used to apply a constant current or potential to the conducting polymer porous film. In certain such embodiments, the measuring signal is a change in potential or current, respectively.

The electrode array can include a pair of electrodes (a positive electrode and a negative electrode) or a plurality of said pairs of electrodes. The electrode array can further comprise patterned electrodes, for example, interdigitated electrodes. In some embodiments, the electrode array includes a plurality of sets of interdigitated electrodes. The interdigitated electrodes can have any shape known in the art, such as, but not limited to circular or rectangular shapes (as shown, for example, in FIG. 1). Alternatively, the electrode array may include a source and a drain electrode separated from one another by a source-drain gap. The electrode array may further comprise a gate electrode wherein the electric signal may be indicative of a certain property of the conducting polymer film under the influence of a gate voltage.

The electrode array can comprise any metal having high conductivity. When a p-type doped conducting polymer is used in a VOCs sensor, preferred electrode metals are those having high work function, which facilitates formation of ohmic contact between the electrodes and the p-type polymer film in the metal-semiconductor interface. For n-type polymer, metals with low work function are preferable. The importance of the ohmic contact is that any variation in the electric signal transmitted by the electrode of VOCs sensor originates from the conducting polymer film and not from the interface barriers. Non-limiting examples of metals suitable for use in the electrode array of VOCs sensor the present invention include Au, Ti, Cu, Ag, Pd, Pt, Ni, Al. In certain embodiments, the metal is selected from Au, Ti, Pt, Pd and combinations thereof. In some exemplary embodiments, the electrode array comprises Au and/or Ti.

Conducting Polymer Porous Film

The term "conducting polymer", as used in various embodiments, refers to a polymer which is intrinsically electrically-conductive, and which does not require incorporation of electrically-conductive additives (e.g., carbon black, carbon nanotubes, metal flake, etc.) to support substantial conductivity of electronic charge carrier. In further embodiments, the term "conducting polymer" refers to a polymer which becomes electrically-conductive following doping with a dopant. In certain embodiments, said doping comprises protonation (also termed herein "protonic doping"). In still further embodiments, the term "conducting polymer" refers to a polymer which is electrically-conductive in the protonated state thereof, wherein said protonation is either partial or full. Alternatively, conducting polymers can be doped via a redox reaction. In yet further embodiments, the term "conducting polymer" refers to a polymer which is electrically-conductive in the oxidized and/or reduced state thereof. The conducting polymers suitable for use in the platform unit of the present invention can have conductivity of a metal or of a semiconductor, ranging from about 0.001 S·cm$^{-1}$ to about 100 S·cm$^{-1}$.

Conducting polymer are typically nitrogen-containing aromatic polymers (such as, but not limited to, polyaniline and polypyrrole (PPy) or sulfur-containing aromatic polymers (e.g., polythiophene, poly(3,4-ethylenedioxythiophene), and poly(p-phenylene sulfide) (PPS), and derivatives, and copolymers thereof. Another type of a conducting polymer includes a linear-backbone with double bonds, such as, for example, polyacetylene. In some embodiments of the present invention the conducting polymer is selected from polyaniline, polythiophene, poly(3,4-ethylenedioxythiophene)-poly(styrene-sulfonate) (PEDOT:PSS), polypyrrole, polydiketopyrrolopyrrole, and derivatives and combinations thereof.

In some exemplary embodiments, the polymer is PANI.

PANI can be protonically doped with a dopant, preferably an acidic dopant. Non-limiting examples of suitable dopants include sodium bisulfite, salicylic acid, maleic acid, fumaric acid, benzoic acid and phosphoric acid. Protonical doping of PANI can be performed by contacting PANI film with an acid, which can be in a form of a vapor, a liquid or a solution. Each possibility represents a separate embodiment of the invention.

In some embodiments, the conducting polymer film has at least one non-uniform surface. In certain embodiments, the conducting polymer film has two non-uniform surfaces. In further embodiments, the conducting polymer film has a top non-uniform surface. In still further embodiments, the conducting polymer film has a bottom non-uniform surface. In some embodiments, said non-uniform surface comprises wrinkles. In some exemplary embodiments, the VOCs sensor comprises protonically doped PANI film having wrinkles on at least one of its surfaces. Without wishing to being bound by theory or mechanism of action, it is contemplated that wrinkles on the PANI film surface are present due to the volume expansion during the doping process. Without further wishing to being bound by theory or mechanism of action, it is suggested that the presence of wrinkles on the conducting polymer film surface provides insensitivity of the film to lateral strain. Said lateral strain insensitivity allows the use of said films as VOCs sensors on flexible substrates.

In some embodiments, the surface coverage by the wrinkles of the at least one non-uniform surface ranges from about 1% to about 10%. In further embodiments, the surface coverage by the wrinkles of the at least one non-uniform surface ranges from about 2% to about 9%, from about 3% to about 8%, or from about 4% to about 7%. Each possibility represents a separate embodiment of the invention.

In some embodiments, the conducting polymer porous film generates an electric signal in response to a chemical reaction between an analyte VOC and the film, which alters the doping state of the polymer. In some embodiments, the doping level of the polymer is changed following protonation or deprotonation of the polymer. In other embodiments, the doping level is changed by electron transfer from or to the analyte VOC. Said protonation, deprotonation and electron transfer (including partial charge transfer) can cause the changes in resistance and/or work function of the conducting material, thereby generating the electric signal of the sensor and providing detection of the analyte VOC.

In some embodiments, the signal is produced by the adsorption and/or absorption of the analyte VOC on and/or into the conducting polymer film. For a pure conducting polymer, inserting analyte molecule into polymer matrix generically increases interchain distance, which affects the electron hopping between different polymer chains and thus affects the polymer conductivity. In some embodiments, the signal is produced by swelling and/or change in crystalline structure of the polymer film as a result of the analyte VOC sorption.

In some embodiments, the conductivity of the conductive polymer porous film ranges from about 0.001 $S*cm^{-1}$ to about 100 $S*cm^{-1}$. In further embodiments, the conductivity of the conductive polymer porous film ranges from about 0.01 $S*cm^{-1}$ to about 10 $S*cm^{-1}$, or from about 0.1 $S*cm^{-1}$ to about 1 $S*cm^{-1}$. In certain embodiments, the conductivity of the doped PANI porous film ranges from about 0.001 $S·cm^{-1}$ to about 100 $S*cm^{-1}$.

In some embodiments the conducting polymer porous film has a vertically ordered porous structure. In certain embodiments, the conducting polymer porous film has pores which transverse the entire thickness of the film (i.e., the pores extend from bottom 107a to top 107b of conductive polymer porous film 107 as schematically shown in FIG. 1). In some embodiments, the conducting polymer porous film has a substantially uniform distribution of pores. The pore structure of the film can be controlled during preparation of said film, for example, by templated coating.

In some embodiments, the conducting polymer porous film has a mean pore size ranging from about 20 nm to about 500 nm. In further embodiments, the conducting polymer porous film has a mean pore size ranging from about 50 nm to about 250 nm, or from about 100 nm to about 200 nm. Each possibility represents a separate embodiment of the invention. In certain embodiments, the conducting polymer porous film has a mean pore size of at least about 50 nm, of at least about 75 nm or at least about 100 nm. Each possibility represents a separate embodiment of the invention.

In some embodiments, the conducting polymer porous film has a porosity ranging from about 30% to about 80% of the total film volume. In further embodiments, the conducting polymer porous film has a porosity ranging from about 40% to about 70% of the total film volume. In certain embodiments, the conducting polymer porous film has a porosity of at least about 30%, at least about 40% or at least about 50%. Each possibility represents a separate embodiment of the invention.

In some embodiments, the conducting polymer porous film has a thickness ranging from about 50 nm to about 300 nm. In further embodiments, the conducting polymer porous film has a thickness ranging from about 100 nm to about 200 nm. The thickness of the conducting polymer porous film is defined as the distance between bottom side 107a and top side 107b of conductive polymer porous film 107 in FIG. 1.

The conducting polymer porous film can have any shape suitable for electrically contacting the electrode array and being supported by the first porous membrane. Non-limiting suitable shapes include rectangular, square and disc shapes.

The VOCs sensor can be configured in a form selected from the group consisting of a resistive sensor, a capacitive sensor, an impedance sensor, a field effect transistor sensor, and combinations thereof. In certain embodiments, VOCs sensor can be configured in a form of a resistive sensor.

The VOCs sensor according to the principles of the present invention can further be used for pressure and/or temperature sensing. It has been surprisingly found by the inventors that the conductive polymer films, doped with various acids, were responsive not only to VOCs, but also to pressure and temperature. The inventors have further found that VOCs and temperature sensing and VOCs and pressure sensing can be decoupled. One of skill in the art readily understands that a signal generated by each parameter (presence of VOCs, pressure or temperature) can be extracted using pre-measurement calibration, post-measurement calculation, a suitable algorithm or a combination thereof.

The Pressure and Temperature Sensor

In some embodiments, the platform unit further comprises at least one temperature and/or pressure sensor. In some embodiments, the platform unit comprises a pressure and temperature sensor having dual sensing sensitivities.

In some embodiments, the pressure and/or temperature sensor comprises conductive nanostructures. The term "nanostructures" should be understood to include structures of different shapes, such as, e.g., nanoparticles, nanosheets, nanotubes, nanowires, or nanorods, having a mean length in the longest dimension thereof in the range of above 1 nm but below 1000 nm.

The conductive nanostructures can include metal nanoparticles. Suitable metal nanoparticles within the scope of the present invention include, but are not limited to Au, Ag, Ni, Co, Pt, Pd, Cu, Al, Zn, Fe, and combinations thereof, including metal alloys such as, but not limited to Au/Ag, Au/Cu, Au/Ag/Cu, Au/Pt, Au/Pd, Au/Ag/Cu/Pd, Pt/Rh, Ni/Co, and Pt/Ni/Fe. Each possibility represents a separate embodiment of the present invention. In certain embodiments, said nanoparticles include gold nanoparticles.

The metal nanoparticles may have any desirable geometry including, but not limited to a cubic, a spherical, and a spheroidal geometry. Each possibility represents a separate embodiment of the present invention.

The term "nanoparticles" should be understood to include particles having a mean particle size in the range of above 1 nm but below 1000 nm. According to some embodiments, the metal nanoparticles have a mean particle size in the range of about 1 nm to about 10 nm. In further embodiments, the metal nanoparticles have a mean particle size in the range of about 2 nm to about 6 nm.

In some embodiments, the metallic nanoparticles are capped with an organic coating. The organic coating of the metal nanoparticles can comprise a monolayer or multilayers of organic molecules. Suitable coating includes, but is not limited to alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, and combinations and derivatives thereof. Each possibility represents a separate embodiment of the present invention.

The conductive nanostructures can include carbon-based nanostructures. The carbon-based nanostructures can be selected from unordered nanostructures (OD), one-dimensional nanostructures (1D), two-dimensional nanostructures (2D) nanostructures and combinations thereof. In certain embodiments, the carbon-based nanostructures are selected from the group consisting of carbon powder, carbon nanotubes and graphite. Each possibility represents a separate embodiment of the invention. In certain embodiments, the carbon nanotubes are single walled carbon nanotubes.

The pressure and/or temperature sensor can further include a polymer. In some embodiments, said nanostructures are dispersed in a polymer. In certain embodiments, the dispersion of the nanostructures inside the polymer is substantially uniform. The term "uniform distribution", as used herein denotes that the volume percentage of the nanostructures varies from one portion of the polymer to another by less than about 40%, less than about 20% or less than about 10%. Each possibility represents a separate embodiment of the invention.

In some embodiments, the weight percent of the conductive nanostructures in the polymer ranges from about 60% to about 90%. In further embodiments, the weight percent of the conductive nanostructures in the polymer ranges from about 70% to about 80%.

The polymer can be any polymer, which allows incorporation therein of a substantial amount of conductive nanoparticles to impart conductivity to the polymer. The polymer should also be suitable for forming a porous and substantially flexible film. In some currently preferred embodiments, the polymer is a self-healing polymer. Thus, in some embodiments, the sensing platform unit according to the principles of the invention comprises a pressure and temperature sensor comprising a self-healing porous film comprising a self-healing polymer and conductive nanostructures.

Various spontaneously self-healing polymers are known in the art, based, for example, on embedded microencapsulated healing agents, supramolecular self-assembly, transition metal thiolates or aromatic disulfides interactions. The self-healing of the self-healing polymers can proceed, inter alia, through dissociation and recombination of dynamic covalent or weak hydrogen bonds at a room temperature. According to some embodiments, the self-healing polymer is a dynamically covalently crosslinked polymer, which crosslinking bridges comprise disulfide moieties. According to further embodiments, the self-healing polymer is crosslinked through aromatic disulfide moieties. In certain such embodiments, the dynamic crosslinking of the polymeric chains can proceed through the metathesis reaction of aromatic disulfides.

According to some embodiments, the polymeric chain comprises a polyurethane. The polyurethane can have a molecular weight in the range from about 250 to about 400 g/mole. The polymeric chain can further comprise an urea unit. Thus, in some embodiments, the polymeric chain comprises a poly(urea-urethane).

According to further embodiments, the polymeric chain comprises a polyether backbone segment. In certain embodiments, the poly(urea-urethane) comprises a polyether backbone segment. In further embodiments, the polyether backbone segment has an average molecular weight of at least about 2000 g/mole. In additional embodiments, the average molecular weight of the polyether backbone segment is in the range of about 2000 to 10,000 g/mole. In certain embodiments, the average molecular weight is from about 2000 to about 6000 g/mole. The polyether segment can be selected from polypropylene glycol or polyethylene glycol. Each possibility represents a separate embodiment of the invention.

According to some embodiments, the polymeric chain comprises an aromatic urethane unit. In certain embodiments, poly(urea-urethane) comprises an aromatic urethane unit. In further embodiments, said aromatic urethane unit is tolylene urethane. According to some embodiments, the polymeric chain comprises an urea unit. In certain embodiments, poly(urea-urethane) comprises an urea unit. In further embodiments, the polymeric chain is covalently bound to the crosslinking bridge through an urea unit. According to some embodiments, the polymeric chains are further dynamically connected via hydrogen bonds between the urea units of the polymeric chains.

According to some exemplary embodiments, the self-healing polymer is poly(propylene-urethaneureaphenyl-disulfide). According to additional embodiments, the self-healing polymer is poly(urethane-carboxyphenyl-disulfide).

In other embodiments, the self-healing polymer is a dynamically crosslinked polymer, in which dynamic crosslinking of the polymeric chains proceeds through hydrogen bonds. In further embodiments, the hydrogen bonds are formed between methacrylate polymeric chains and amine functional group. In certain embodiments, the self-healing polymer is poly(2-hydroxypropyl methacrylate)/poly(ethyleneimine).

In some embodiments, the self-healing porous film has conductivity ranging from about 0.0000001 $S \cdot cm^{-1}$ to about 1 $S \cdot cm^{-1}$. In further embodiments, the self-healing porous film has conductivity ranging from about 0.000001 $S \cdot cm^{-1}$ to about 0.1 $S \cdot cm^{-1}$, or from about 0.00001 $S \cdot cm^{-1}$ to about 0.01 $S \cdot cm^{-1}$. Each possibility represents a separate embodiment of the invention.

In some embodiments, the self-healing porous film comprises nanofibers. The thickness of the nanofibers can range from about 100 nm to about 5 μm. In further embodiments, the thickness of the nanofibers ranges from about 200 nm to about 2.5 μm, or from about 500 nm to about 1 μm. Each possibility represents a separate embodiment of the invention. In certain embodiments, said nanofibers are polymer nanofibers In some embodiments, the self-healing porous film has a mean pore size ranging from about 20 nm to about 20 μm. In further embodiments, the self-healing porous film has a mean pore size ranging from about 50 nm to about 10 μm, from about 100 nm to about 5 μm, from about 200 nm to about 2.5 μm or from about 500 nm to about 1 μm. Each possibility represents a separate embodiment of the invention.

In some embodiments, the self-healing porous film has a porosity ranging from about 30% to about 80% of the total film volume. In further embodiments, the self-healing porous film has a porosity ranging from about 40% to about 70% of the total film volume.

The thickness of the self-healing porous film can range from about 100 nm to about 5 μm. In further embodiments, the self-healing porous film has a thickness ranging from about 500 nm to about 2 μm.

In some embodiments, the pressure and temperature sensor is insensitive to the VOCs adsorption.

The pressure and temperature sensor can be configured in a form of a resistive sensor.

The pressure and temperature sensor can further comprise an electrode array, being in electric contact with said electrode array. The electrode array can be similar to the electrode array of the VOCs sensor. In some embodiments, said electrode arrays are different.

The electrode array of the pressure and temperature sensor can include a pair of electrodes (a positive electrode and a negative electrode) or a plurality of said pairs of electrodes. The electrode array can further comprise patterned electrodes, for example, interdigitated electrodes. In some embodiments, the electrode array includes a plurality of interdigitated electrodes sets. The interdigitated electrodes can have any shape known in the art, such as, but not limited to circular or rectangular shapes (as shown, for example, in FIG. 2).

The electrode array can comprise any metal having high conductivity. Non-limiting examples of metals suitable for use in the electrode array of the pressure and temperature sensor include Au, Ti, Cu, Ag, Pd, Pt, Ni, Al, and combinations thereof. In some exemplary embodiments, the electrode array comprises Au and/or Ti.

The electrode array can be disposed above, below or adjacent to the self-healing polymer film comprising conductive nanostructures. Each possibility represents a separate embodiment of the invention.

Second Porous Membrane

According to some embodiments, the platform unit further comprises a second porous membrane. The second porous membrane can be disposed between the VOCs sensor and the pressure and temperature sensor. In particular embodiments, said membrane is electrically insulating.

The second porous membrane acts as a separator between the VOCs sensor and the pressure and temperature sensor. In certain embodiments, the second porous membrane prevents electric contact between the VOCs sensor and the pressure and temperature sensor.

The second porous membrane can be made of any suitable polymeric material, which can be formed into a porous and substantially flexible film.

The second porous membrane can include a polymer selected from a fluoropolymer, aromatic polymer, polyamide, aramide and combinations, and derivatives thereof. Non-limiting examples of polymers suitable for use in the second porous membrane of the platform unit include polyvinylidene difluoride, (PVDF), Poly(vinylidene fluoride-co-hexafluoropropylene) (PVDF-HFP), polystyrene (PS), Nylon and combinations thereof.

The second membrane is characterized by high porosity in order to allow VOCs desorption from the VOCs sensor, preventing accumulation of the VOCs therein. In some embodiments, the second porous membrane has a mean pore size ranging from about 20 nm to about 20 µm. In further embodiments, the second porous membrane has a mean pore size ranging from about 50 nm to about 10 µm, from about 100 nm to about 5 µm, from about 200 nm to about 2 µm or from about 500 nm to about 1 µm. Each possibility represents a separate embodiment of the invention.

In some embodiments, the second porous membrane has a porosity ranging from about 30% to about 90% of the total membrane volume. In further embodiments, the second porous membrane has a porosity ranging from about 40% to about 80%, or from about 50% to about 70%, of the total membrane volume.

According to some embodiments, the second porous membrane comprises polymer nanofibers. The mean thickness of a nanofiber of the second porous membrane can range from about 100 nm to about 1 µm. In certain embodiments, the mean thickness of a nanofiber of the second porous membrane ranges from about 200 nm to about 500 nm. According to further embodiments, the second porous membrane is prepared by electrospinning.

The thickness of the second porous membrane is preferably relatively low, in order to keep the total thickness of the platform unit low. In some embodiments, the second porous membrane has a thickness ranging from about 100 nm to about 1 µm. In further embodiments, the second porous membrane has a thickness ranging from about 200 nm to about 500 nm.

The shape of the second porous membrane is chosen to provide effective separation between the sensors.

Third Porous Membrane

According to some embodiments, the platform unit further comprises a third porous membrane. In further embodiments, the third porous membrane substantially covers the pressure and temperature sensor. In other embodiments, the third porous membrane substantially covers the VOCs sensor. In certain embodiments, the third porous membrane is hydrophobic. In additional embodiments, the third porous membrane is self-cleaning. In certain embodiments, the third porous membrane has a rough surface. The term "rough", as used herein, refers in some embodiments, to the roughness ranging from about 200 nm to about 5 µm. In further embodiments, the term "rough" refers to a roughness ranging from about 500 nm to about 2 µm. Without wishing to being bound by theory or mechanism of action, it is contemplated that the roughness of the third porous membrane surface provides the self-cleaning ability. The third porous membrane acts as a protective layer of the pressure and temperature sensor or the VOCs sensor. In certain embodiments, the third porous membrane prevents contamination of the sensors.

The third porous membrane can be made of any suitable polymeric material, which can be formed into a porous and substantially flexible film. The third porous membrane can include a polymer selected from a fluoropolymer, aromatic polymer, polyamide, aramide and, and derivatives combinations thereof. Non-limiting examples of polymers suitable for use in the third membrane of the platform unit include polyvinylidene difluoride, (PVDF), Poly(vinylidene fluoride-co-hexafluoropropylene) (PVDF-HFP), polystyrene (PS), Nylon and combinations thereof.

In some embodiments, the third porous membrane has a mean pore size ranging from about 20 nm to about 20 µm. In further embodiments, the third porous membrane has a mean pore size ranging from about 50 nm to about 10 µm, from about 100 nm to about 5 µm, from about 200 nm to about 2 µm or from about 500 nm to about 1 µm. Each possibility represents a separate embodiment of the invention.

In some embodiments, the third porous membrane has a porosity ranging from about 30% to about 90% of the total membrane volume. In further embodiments, the third porous membrane has a porosity ranging from about 40% to about 80%, or from about 50% to about 70%, of the total membrane volume.

According to some embodiments, the third porous membrane comprises polymer nanofibers. The mean thickness of a nanofiber of the third porous membrane can range from about 200 nm to about 5 µm. In certain embodiments, the mean thickness of a nanofiber of the third porous membrane ranges from about 500 nm to about 2 µm. According to further embodiments, the third porous membrane is prepared by electrospinning.

The thickness of the third porous membrane is preferably relatively low, in order to keep the total thickness of the platform unit low. In some embodiments, the third porous membrane has a thickness ranging from about 200 nm to about 5 µm. In further embodiments, the third porous membrane has a thickness ranging from about 500 nm to about 2 µm.

The shape of the third porous membrane is chosen to provide effective coverage of the sensors pressure and temperature sensor and/or VOCs sensor.

The Platform Unit

In various embodiments, there is provided a vapor-permeable flexible sensing platform unit comprising: a first porous membrane, wherein said membrane is substantially flexible and hydrophobic; and a volatile organic compounds (VOCs) sensor disposed on said membrane.

In some embodiments there is provided a vapor-permeable flexible sensing platform unit comprising: a first porous membrane, wherein said membrane is substantially flexible and hydrophobic; a VOCs sensor disposed on said membrane; and a pressure and temperature sensor. The pressure and temperature sensor can include a self-healing porous film comprising a self-healing polymer and conductive nanostructures. In certain embodiments, the nanostructures are selected from metallic nanoparticles capped with an organic coating and carbon-based nanostructures. The pressure and temperature sensor can further include an electrode array. In further embodiments, the sensing unit further comprises a second porous membrane disposed between the VOCs sensor and the pressure and temperature sensor. In particular embodiments, the second porous membrane is electrically insulating. In still further embodiments, the sensing platform unit comprises a third porous membrane substantially covering the pressure and temperature sensor. In certain embodiments, the third porous membrane is hydrophobic. In additional embodiments, the third porous membrane is self-cleaning.

In some embodiments there is provided a vapor-permeable flexible sensing platform unit comprising: a first porous membrane, wherein said membrane is substantially flexible and hydrophobic; a volatile organic compound (VOC) sensor disposed on said membrane; a pressure and temperature sensor comprising a self-healing porous film comprising a self-healing polymer and conductive nanostructures selected from metallic nanoparticles capped with an organic coating and carbon-based nanostructures; a second porous second porous membrane disposed between the VOCs sensor and the pressure and temperature sensor; and a third porous substantially covering the pressure and temperature sensor. In particular embodiments, the second porous membrane is electrically insulating, and/or the third porous membrane is hydrophobic and/or self-cleaning.

In some embodiments, at least two of the first porous membrane, the second porous membrane and the third porous membrane are made of the same material and/or have the same porosity. In some embodiments, the first porous membrane, the second porous membrane and the third porous membrane are made of the same material and/or have the same porosity. In other embodiments, the first porous membrane, the second porous membrane and the third porous membrane are made of different materials and/or have different porosities.

Figure 2:
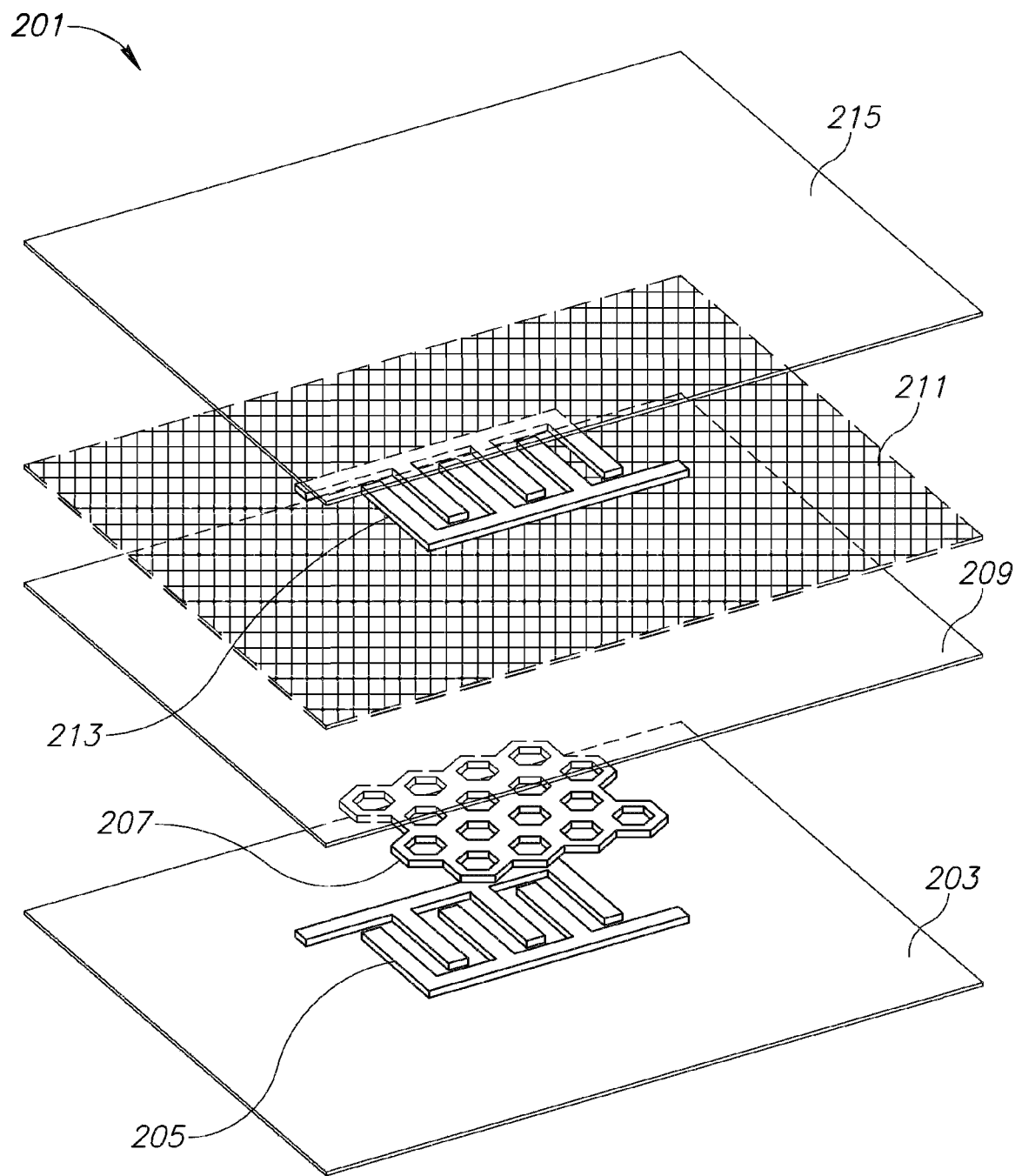
FIG. 2: A schematic exploded view of the vapor-permeable flexible sensing platform unit comprising a first porous membrane, a VOCs sensor, a second porous membrane, a pressure and temperature sensor and a third porous membrane, according to some embodiments of the invention.

FIG. 2 schematically represents an exploded view of the platform unit 201, according to some embodiments of the invention. Platform unit 201 includes first porous membrane 203, electrode array 205, conducting polymer porous film 207, second porous membrane 209, pressure and temperature sensor 211 comprising electrode array 213, and third porous membrane 215. Electrode array 205 is disposed on first porous membrane 203 and conducting polymer porous film 207 is disposed on electrode array 205, being in electrical contact therewith. Combination of electrode array 205 and conducting polymer porous film 207 forms a VOCs sensor. Second porous membrane 209 is disposed between conducting polymer porous film 207 and pressure and temperature sensor 211 comprising and electrically connected to electrode array 213. Third porous membrane 215 is disposed on pressure and temperature sensor 211, substantially covering thereof and protecting platform unit 201 from contamination.

In some embodiments, the sensing platform unit comprises a first porous membrane, wherein said membrane is substantially flexible and hydrophobic; a volatile organic compound (VOC) sensor disposed on said membrane; and a third porous membrane substantially covering the VOCs sensor.

One of the advantages of the platform unit of the present invention is that while having multiple sensing properties and having various functionalities, such as, for-example, self-healing and self-cleaning, the thickness thereof is relatively low, thus being particularly suitable for use in electronic and artificial skin applications. Accordingly, in some embodiments, the platform unit according to the principles of the invention has a thickness below about 1000 µm. In further embodiments, the platform unit according to the principles of the invention has a thickness below about 900 µm, below about 800 µm, below about 700 µm, below about 600 µm, below about 500 µm, or below about 400 µm. Each possibility represents a separate embodiment of the invention.

In some embodiments, the thickness of the platform unit is defined as a distance between the bottom side of the first porous membrane and the top side of the VOCs sensor, for example the top side of the conducting polymer porous film. In certain such embodiments, the thickness of the platform unit is defined as a distance between bottom side 103a of first porous membrane 103 and top side 107b of conducting polymer porous film 107, as schematically depicted in FIG. 1.

In some embodiments, the thickness of the platform unit is defined as a distance between the bottom side of the first porous membrane and the top side of the pressure and temperature sensor.

In some embodiments, the thickness of the platform unit is defined as a distance between the bottom side of the first porous membrane and the top side of the third porous membrane. In certain embodiments, the thickness of the platform unit is defined as a distance between the bottom side of first porous membrane 203 and the top side of third porous membrane 215, as schematically depicted in FIG. 2.

In some embodiments, the platform unit according to the principles of the invention is integrated on electronic or artificial skin surface. Each possibility represents a separate embodiment of the invention.

The platform unit according to the principles of the present invention is configured to provide the detection of the presence and concentration of the analyte molecules in the surrounding environment. According to some embodiments, the platform unit is for use in monitoring health of a subject, comprising detecting VOCs emitted or excreted from skin of the subject by the VOCs sensor. In further embodiments, the platform unit is for use in monitoring health of a subject, comprising detecting VOCs emitted from breath of the subject by the VOCs sensor. The platform unit can be placed on a skin surface of a subject, wherein the first porous membrane contacts the skin surface.

Non-limiting examples of analytes, which can be detected by the platform unit include VOCs selected from 1-hexanal, 1-hexanol, cyclohexanone and 2-hexanone. Various VOCs are indicative of different diseases. Thus, the platform unit can provide the detection of a volatile organic compound indicative of a disease, a disorder or a condition in a subject.

In some embodiments, the platform unit is configured to detect humidity.

In some embodiments, the platform unit is configured to detect pressure. In some embodiments, the platform unit is configured to detect temperature.

Sensor Signal Measurement and Analyzing Devices

The signal of the VOCs sensor and/or pressure and temperature sensor can be detected and/or measured by a suitable detection device. Thus, in some embodiments, the platform unit or its sensor is coupled to the signal detection and/or measuring device. Suitable detection and/or measuring devices should be susceptible to a change in any one or more of resistance, conductance, alternating current (AC), frequency, capacitance, impedance, inductance, mobility, electrical potential, piezoelectricity, and voltage threshold. Each possibility represents a separate embodiment of the present invention. In certain embodiments, the detection and/or measuring device is susceptible to a change in resistance or conductance of the sensors. In additional embodiments, the measuring devices are susceptible to swelling or aggregation of conducting polymer and/or conductive nanostructures. Each possibility represents a separate embodiment of the present invention. Changes in the electric properties of the sensor(s), such as resistance, conductance, direct or alternating current, capacitance, impedance, electrical potential, or voltage threshold can be measured by any suitable device known in the art, including, inter alia, a data logger, a potentiostat, a voltmeter, a conductivity meter, an LCR meter or a millimeter. Changes in the piezoelectricity properties of the sensor set can be measured using, for example, a piezoelectric sensor. The measured signals can be displayed on a display or transmitted to a host computer.

When sensors having dual or multiple sensing sensitivities or a plurality of sensors are used, the signals obtained from the sensors can be analyzed by a computing system configured for executing various algorithms stored on a non-transitory memory. For example, if the VOCs sensor according to the principles of the present invention is also sensitive to temperature and/or pressure, the response of the sensor to the VOCs can be decoupled from the response thereof to temperature and/or pressure using said algorithms. Thus, according to some embodiments, the self-healing platform unit is coupled to said computing system. The algorithms can include learning and pattern recognition algorithms, such as, but not limited to, artificial neural network (ANN) algorithm, support vector machine (SVM), discriminant function analysis (DFA), principal component analysis (PCA), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, nearest neighbor, Fisher linear discriminant analysis (FLDA), soft independent modeling of class analogy (SIMCA), K-nearest neighbors (KNN), genetic algorithms, and fuzzy logic algorithms and canonical discriminant analysis (CDA).

In some embodiments, the decoupling of the response of the sensor to different stimuli is based on the difference in the response amplitude to different types of stimuli. In further embodiments, the response of the VOCs sensor of the invention to the detection of VOCs is significantly different than the response thereof to temperature and/or pressure. A statistically significant difference can be determined by any test known to the person skilled in the art. Common tests for statistical significance include, among others, t-test, ANOVA1 Kruskal-Wallis, Wilcoxon, Mann-Whitney and odds ratio.

Platform Unit Fabrication Procedure

According to some aspects and embodiments of the invention there is provided a method for fabricating the vapor-permeable flexible sensing platform unit comprising a first porous membrane, wherein said membrane is substantially flexible and hydrophobic; and a volatile organic compounds (VOCs) sensor disposed on said membrane, the VOCs sensor comprising an electrode array and a conducting polymer porous film being in electric contact with said electrode array, wherein the VOCs sensor is insensitive to lateral strain, the method comprising: providing a first porous membrane which is substantially flexible and hydrophobic; forming an electrode array; providing a conducting polymer porous film; and disposing said film on the electrode array or the first porous membrane, wherein the film is in electric contact with the electrode array, thereby forming the VOCs sensor.

According to some embodiments, the electrode array is formed on the first porous membrane and the conducting polymer porous film is disposed on said electrode array. According to some embodiments, the electrode array is formed on the first porous membrane and the conducting polymer porous film is disposed adjacently to said electrode array. According to some embodiments, the conducting polymer porous film is disposed on the first porous membrane and the electrode array is formed on said conducting polymer porous film.

The method according to the principles of the present invention can further comprise a step of forming a second porous membrane on the conducting polymer porous film or on the electrode array of the VOCs sensor.

In some embodiments, the method of the present invention further comprises a step of forming a pressure and temperature sensor. In certain embodiments, the step of forming a pressure and temperature sensor comprises forming a self-healing film. Said step can be effected by mixing a self-healing polymer and conductive nanostructures. In certain embodiments, the conductive nanostructures are selected from metallic nanoparticles capped with an organic coating; carbon-based nanostructures; and combinations thereof. The step can further include applying said mixture onto the second porous membrane, thereby forming a pressure and temperature sensor. In some embodiments, the step of forming a pressure and temperature sensor further comprises forming an electrode array on top of, below or adjacent to the self-healing polymer film comprising conductive nanostructures. Accordingly, in certain embodiments, the step of forming a pressure and temperature sensor comprises forming an electrode array on the second porous membrane. In certain embodiments, the step of forming a pressure and temperature sensor comprises forming an electrode array on the self-healing polymer film comprising conductive nanostructures.

In further embodiments, the method of the invention comprises forming a third porous membrane substantially covering the pressure and temperature sensor or the VOCs sensor. The third membrane can be formed by applying a solution of a polymer powder onto the self-healing film or the conducting polymer film. Each possibility represents a separate embodiment of the invention.

Preparation of the Conducting Polymer Film

Various techniques can be used to prepare conducting polymer films. Non-limiting examples include, spin-coating, dip-coating, drop-coating, and screen printing. spin-coating, dip-coating, drop-coating, and screen printing.

Spin-coating: Spin-coating is a simple method for preparing films from soluble conducting polymers. In this process, the conducting polymer solution is spread on a rotating substrate. After evaporation of solvent, a thin film is formed. Thickness of the film can be controlled, inter alia, by repeating the above process. Concentration of the solution and rotating rate of the substrate also play important roles in adjusting the thickness of the formed film. Said method can be used to prepare conducting polymer films on both conducting and insulating substrates.

Dip-coating: When dipping a substrate into a chemical polymerization solution, part of the polymer will be deposited onto its surface. This process occurs on different substrates, and the thickness of the film is usually controlled by dipping time. Another similar process involves alternatively immersing a substrate into the monomer and oxidant solutions. The adsorbed monomer is polymerized on the surface of substrate.

Drop-coating: A polymer solution is drop dried or drops of a monomer and oxidant solutions are dropped and reacted on a substrate.

Screen printing: Screen printing can be used for producing thin films from soluble conducting polymers.

As mentioned hereinabove, the conducting polymer useful in the method of preparation of the platform unit can be selected from, but not limited to, polyaniline, polypyrrole, polydiketopyrrolopyrrole, polythiophene, poly(3,4-ethylenedioxythiophene), poly(p-phenylene sulfide), polyacetylene and derivatives, and copolymers thereof. In certain embodiments, the conducting polymer is PANI.

Inventors of the present invention have developed an eco-friendly method for preparing a conducting polymer film, which can be supported on any substrate, including polymeric and organic substrates, or, alternatively, can be a free-standing film. Said method is particularly suitable for the preparation of PANI conducting films.

A Lift-Off, Float-On (LOFO) Method for the Preparation of a Protonically Doped Polyaniline Film In some aspects and embodiments of the invention there is provided a lift-off, float-on (LOFO) method for the preparation of a protonically doped polyaniline (PANI) film, the method comprising the following consecutive steps: (a) applying PANI organic solution onto a rigid inorganic substrate, thereby obtaining a PANI film supported on said substrate; (b) protonically doping the obtained PANI film; (c) contacting the doped PANI film supported on the substrate with a portion of deionized water, thereby separating the doped PANI film from the substrate; (d) dedoping the PANI film by replacing the portion of water, being in contact with the PANI film with an additional portion of deionized water; and (e) protonically doping the dedoped PANI film.

In some embodiments, the LOFO method further comprises step (f) comprising transferring the doped PANI film to a final substrate. In some embodiments, the LOFO method further comprises step (g) comprising drying the doped PANI film supported on the final substrate. In additional embodiments, the LOFO method further comprises step (h) comprising exerting pressure on the doped PANI film for the attachment thereof to the final substrate.

The eco-friendly LOFO method has been developed specifically to allow transfer of the conducting polymer film from the rigid substrate to flexible substrate. Dissolution of PANI powders is generally accomplished with the help of solvents with high cytotoxicity (e.g., cresol, a,a,a-trifluoro-m-cresol, chlorophenol, or trifluoroacetic acid). The only low-toxicity solvent, which can dissolve PANI powder to obtain relatively high concentrations is N-methyl-2-pyrrolidone (NMP). However, NMP can also dissolve many commonly used flexible polymer substrates, thereby preventing their use in the synthesis of PANI films. The LOFO method according to the principles of the present invention is an eco-friendly process, which allows, inter alia, preparing a PANI film on rigid inorganic substrate and transfer thereof to other substrates, including organic and polymeric substrates. Said LOFO method is based on a water transfer. In contrast to the traditional LOFO, which ordinarily needs the assistance of hazard organic solvents or etching solutions (e.g. acetone, acetonitrile, KOH or HF aqueous solution) that can affect the environment and targeted substrate, the LOFO method according to the principles of the invention does not involve the use of an organic solvent and/or an etching solution in transferring the conducting polymer film to the final substrate. The term "etching solution", as used herein, refers in some embodiments, to a solution comprising a mixture of strong acids or strong bases. The term "etching solution", as used herein, refers in other embodiments, to a solution comprising KOH, HF, persulfate ions, perchlorate, ions, peroxide ions, chlorite ions, and combinations thereof.

Figure 3A:
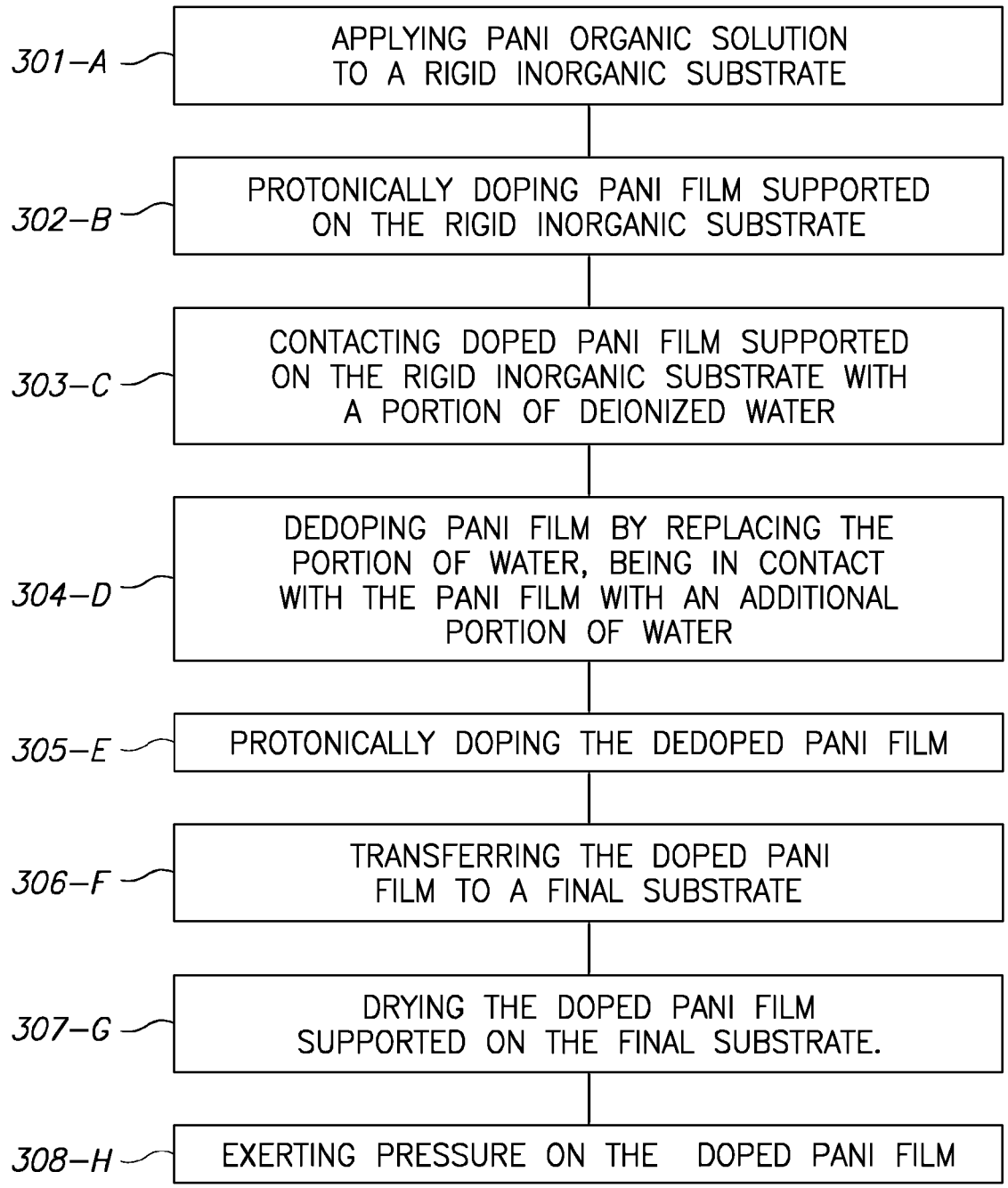
FIG. 3A: A flow chart of the lift-off, float-on (LOFO) method for the preparation of a protonically doped polyaniline (PANI) thin film, according to some embodiments of the invention.
Figure 3B:
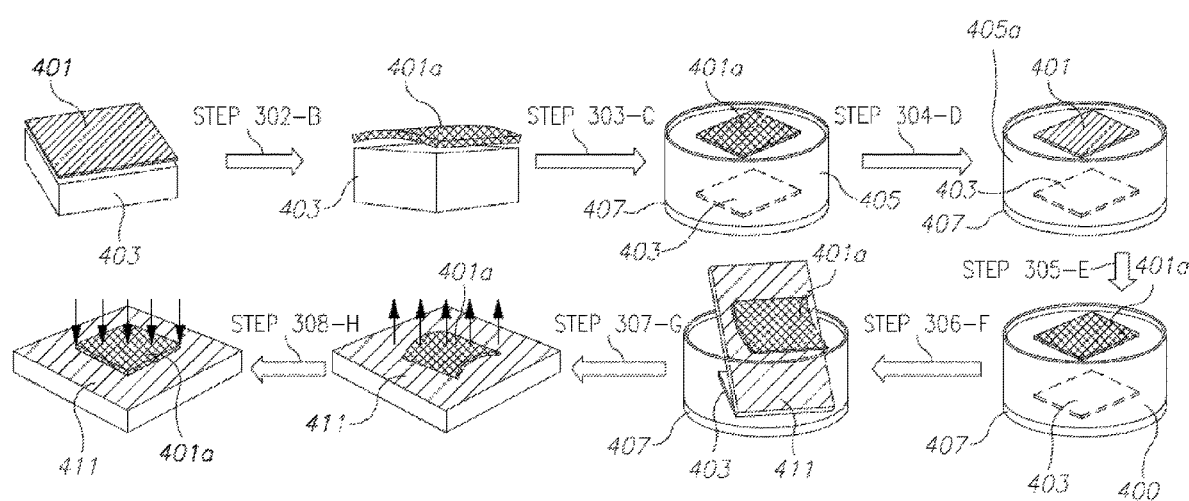
FIG. 3B: Schematic representation of the steps of the LOFO method presented in FIG. 3A.

FIGS. 3A and 3B schematically represent the LOFO method according to some embodiments of the invention.

STEP 301-A: Applying PANI organic solution to rigid inorganic substrate 403, thereby obtaining PANI film 401 supported on rigid inorganic substrate 403.

PANI organic solution can be prepared by dissolving PANI powder in N-methyl-2-pyrrolidone (NMP). PANI powder can be prepared by process known in the art. A non-limiting example of PANI powder synthesis is as follows: aniline, hydrochloric acid and DI water are mixed to form solution A and ammonium persulfate is dissolved in DI water to form solution B. Solution A and B are cool down to 0° C., solution B is dropwise added into solution A under stirring. The reaction continues for 8 hours. The prepared doped PANI powder is rigorously washed with DI water and then immersed into pure ammonia for 12 hours. After filtration and washing with DI water, the PANI powder is soxhlet extracted by toluene, mixture of ethanol and water in sequence to remove oligomer and salt for 72 h under the protection of $N_2$. After vacuum baking overnight, PANI powder is prepared.

In certain embodiments, the concentration of PANI powder in the organic solution ranges from about 0.01 g/ml to about 0.2 g/ml. In certain embodiments, the concentration of PANI powder in the organic solution ranges from about 0.01 g/ml to about 0.05 g/ml or from about 0.01 g/ml to about 0.02 g/ml.

The step of applying PANI organic solution to the rigid inorganic substrate in step (a) can comprise a method selected from spin-coating, dip-coating, drop-coating, and screen printing. In certain embodiments, the step of applying PANI organic solution to the rigid inorganic substrate in step (a) comprises spin-coating. In some embodiments, the spin-coating is performed at a rotating speed ranging from 500 rpm to about 5000 rpm. In further embodiments, the spin-coating is performed for a time period ranging from about 30 seconds to about 20 minutes. In certain embodiments, different rotating speeds are applied for different periods of time to obtain the PANI film. In some exemplary embodiments, the PANI solution is spin-coated at 1000 rpm for about 10 mins and at 3500 rpm for about 30 s. The volume of the applied PANI solution can range from about 10 µl to about 50 µl. In certain embodiments, the step of applying PANI organic solution to the rigid inorganic substrate in step (a) comprises storing the obtained PANI film supported on the rigid inorganic substrate in a vacuum chamber for at least about 8 hours.

The rigid inorganic substrate can be made of a material selected from glass, silicon wafer, sapphire, or quartz. Without wishing to being bound by theory or mechanism of action, good surface wettability of the substrate to water allows water penetration into the interspace between at least partially doped PANI and the substrate to achieve the peel-off of the PANI film. Accordingly, in some currently preferred embodiments, the inorganic rigid substrate has a good water wettability. In some embodiments, the inorganic substrate has a water contact angle of less than about 20°. In further embodiments, the inorganic substrate has a water contact angle of less than about 15°. In still further embodiments, the inorganic substrate has a water contact angle of less than about 10°. In yet further embodiments, the inorganic substrate has a water contact angle of less than about 7.5°. In still further embodiments, the inorganic substrate has a water contact angle of less than about 5°.

In some embodiments, the inorganic substrate has a contact angle with NMP of less than about 20°. In further embodiments, the inorganic substrate has a contact angle with NMP of less than about 15°. In still further embodiments, the inorganic substrate has a contact angle with NMP of less than about 10°. In yet further embodiments, the inorganic substrate has a contact angle with NMP of less than about 5°.

In some embodiments, the LOFO method comprises enhancing the wettability of the rigid inorganic substrate by using a process selected from plasma treatment or strong oxidant liquid treatment. In certain embodiments, the LOFO method comprises plasma treatment of the inorganic rigid substrate. In further embodiments, the plasma comprises $O_2$ and Ar plasma. The plasma treatment can proceed for about 10 to 60 minutes. In certain embodiments, the plasma treatment is performed for about 30 mins.

The inorganic substrate can have a substantially smooth surface or a non-uniform surface. The substrate having a non-uniform surface can be used for the preparation of a porous PANI film.

STEP 302-B: Protonically doping PANI film 401 supported on rigid inorganic substrate 403 to obtain doped PANI film 401a.

In some embodiments, protonically doping the PANI film in step (b) comprises contacting the PANI film with an acid vapor. In some embodiments, protonically doping the PANI film in step (b) comprises contacting the PANI film with an acidic solution. In certain such embodiments, said contacting comprises immersing the PANI film supported on the rigid inorganic substrate in acidic solution or placing the PANI film supported on the rigid inorganic substrate on the solution surface. Non-limiting examples of the acids, which can be used for proton doping include hydrochloric acid, sodium bisulfate, salicylic acid, maleic acid, fumaric acid, benzoic acid, phosphoric acid and any combination thereof. The concentration of the acidic solution can range from about 0.005M to about 10M, such as, for example, from about 0.005M to about 1M, or from about 0.01 M to about 0.1M. Each possibility represents a separate embodiment of the invention.

STEP 303-C: Contacting doped PANI film 401a supported on rigid inorganic substrate 403 with a portion of deionized water 405, thereby separating doped PANI 401a film from rigid inorganic substrate 403.

In certain such embodiments, said contacting comprises immersing the PANI film supported on the rigid inorganic substrate in water or placing the PANI film supported on the rigid inorganic substrate on the water surface. According to some embodiments, doped PANI film 401a is placed in water tank 407, filled with water 405, wherein doped PANI film 401a floats on the water surface.

STEP 304-D: Dedoping PANI film 401a by replacing portion of water 405, being in contact with the PANI film with an additional portion of water 405a to obtain dedoped PANI film 401.

According to some embodiments, the LOFO method includes replacing the portion of water in step (d) for at least two times. According to further embodiments, the LOFO method includes replacing the portion of water in step (d) for at least three times. In still further embodiments, the water is replaced for at least three times in 48 hours.

STEP 305-E: Protonically doping dedoped PANI film 401.

Protonically doping the PANI film in step (e) can comprise contacting the PANI film with acidic solution. In certain such embodiments, said contacting comprises immersing the PANI film in acidic solution or placing the PANI film on the solution surface. In particular embodiments, said contacting comprises removing water 405 from water tank 407 and filling it with acidic solution 409. Non-limiting examples of the acids, which can be used for proton doping include hydrochloric acid, sodium bisulfate, salicylic acid, maleic acid, fumaric acid, benzoic acid, phosphoric acid and any combination thereof. The concentration of the acidic solution can range from about 0.005M to about 10M, such as, for example, from about 0.005M to about 1M, or from about 0.01 M to about 0.1M. Each possibility represents a separate embodiment of the invention.

STEP 306-F: Transferring doped PANI film 401a to final substrate 411.

In some embodiments, said transferring comprises immersing final substrate 411 into water tank 407 and contacting doped PANI film 401a. The final substrate can be selected from the group consisting of a rigid substrate, flexible substrate, continuous substrate, porous substrate, and hollow substrate. Each possibility represents a separate embodiment of the invention. The rigid final substrate can have a substantially flat or a curved surface. The hollow substrate can be used to prepare a substantially free-standing PANI film. In some embodiments, the hollow substrate comprises a frame. When preparing the platform unit according to the principles of the present invention, the final substrate is porous.

The final substrate can be made of any desired material, including polymers, which are unstable in NMP. Non-limiting examples of the substrate materials include polyethylene terephthalate (PET), polyvinylidene difluoride, (PVDF), Poly(vinylidene fluoride-co-hexafluoropropylene) (PVDF-HFP), polystyrene (PS), Poly(styrene-butadiene-styrene) (SBS), and Nylon.

STEP 307-G: Drying doped PANI film 401a supported on final substrate 411.

In some embodiments, the drying step comprises placing the PANI film supported on the final substrate in a vacuum chamber at a pressure of below about 10000 Pa.

STEP 308-H: Exerting pressure on doped PANI film 401a for the attachment thereof to final substrate 411.

In some embodiments, the method comprises increasing the pressure in the vacuum chamber to about 1 Atm or higher.

It should be emphasized that when a simplified approach is used, wherein the doped PANI film is transferred to a water tank, where it is separated from the inorganic rigid support and transferred onto a final subject without the depoping and doping steps (steps (d) and (e), respectively), the concentration of dopant cannot be controlled due to the fast dedoping process of the PANI film in the water tank. In contrast, the LOFO method according to the principles of the present invention beneficially enables preparation of PANI films with controllable doping levels supported on a substrate of choice.

Preparation of the Conducting Polymer Porous Film

According to the principles of the present invention, the conducting polymer film of the VOCs sensor has a porous structure. Accordingly, the method for fabricating the vapor-permeable flexible sensing platform unit comprises the step of providing a conducting polymer porous film. In some embodiments, said step comprises applying a solution of a conducting polymer onto a substrate having a non-uniform surface.

The conducting polymer can be applied onto the substrate having a non-uniform surface by any process as described above, such as, but not limited to, spin-coating or dip-coating.

The non-uniform surface of the substrate can include a pattern. In certain embodiments, said pattern is a sacrificial pattern. The term "sacrificial pattern", as used herein, refers to a pattern, which is configured to be removed from the substrate. In certain embodiments, the pattern has a vertically ordered structure. In some embodiments, the substrate is a rigid substrate. In other embodiments, the substrate comprises a rigid base. The sacrificial pattern can be formed on said rigid base.

In particular embodiments, the substrate comprises an inorganic material. The inorganic material can selected from the group consisting of glass, silicon wafer, sapphire, quartz, and metal oxide. The substrate can comprise a combination of inorganic materials.

In certain embodiments, the substrate comprises nanostructures epitaxially grown thereon. Non-limiting examples of such nanostructures include nanowires, nanorods, nanotubes, and nanoneedles.

The nanostructures can be made of a material, which can be dissolved by an acid. In some embodiments, said material can be dissolved without the use of an organic solvent or an etching solution. Said material can be, for example, a metal oxide. In some embodiments, the nanostructures comprise a material selected from ZnO, $Co_3O_4$, NiO, and $Fe_2O_3$. In some exemplary embodiments, said material is ZnO.

Non-limiting examples of the methods suitable for epitaxially growing the nanostructures on the substrate include aqueous immersion method, chemical vapor deposition, physical vapor deposition, hydrothermal method, solvent thermal method, and electrochemical deposition. Each possibility represents a separate embodiment of the invention. Chemical bath deposition can be performed at a temperature of from about 80 to about 100° C. Typical time periods for the chemical bath deposition are 2-10 hours.

In certain embodiments, the epitaxial growth method comprises a preceding step of depositing a seed layer of nanoparticles on the substrate surface. In further embodiments, the seed layer comprises the same material as the nanostructures on the substrate. The seed layer can be deposited by magnetron sputtering or drop-casting, In some embodiments, the method for epitaxially growing the nanostructures comprises magnetron sputtering. When using magnetron sputtering, commercial metal oxide target, for example ZnO, can be used. The magnetron sputtering power can range from about 50 Watt to about 1000 Watt, such as, for example from about 100 watt to about 750 Watt, or from about 250 Watt to about 500 Watt. Each possibility represents a separate embodiment of the invention. The magnetron sputtering can be performed under inter gas atmosphere, for example under argon atmosphere. In certain embodiments, the magnetron sputtering is performed in radio frequency sputtering mode.

In some embodiments, the method for epitaxially growing the nanostructures comprises drop-casting. Drop-casting can be followed by baking the substrate at the temperature of from about 250 to about 350° C.

In some exemplary embodiments, the substrate comprises epitaxially grown ZnO nanowires. In further embodiments, said ZnO nanowires are grown on a glass substrate.

In some embodiments, the method for epitaxially growing the nanostructures involves the use of an aqueous solution of $Zn(NO_3)_2$ stabilized with Hexamethylenetetramine (HMTA).

In some embodiments, the step of providing a conducting polymer porous film comprises removing the sacrificial pattern from the substrate, while the conducting polymer film remains on the substrate. In further embodiments said step comprises removing the nanostructures from the substrate by a process selected from acid dissolution or etching.

Figure 4A:
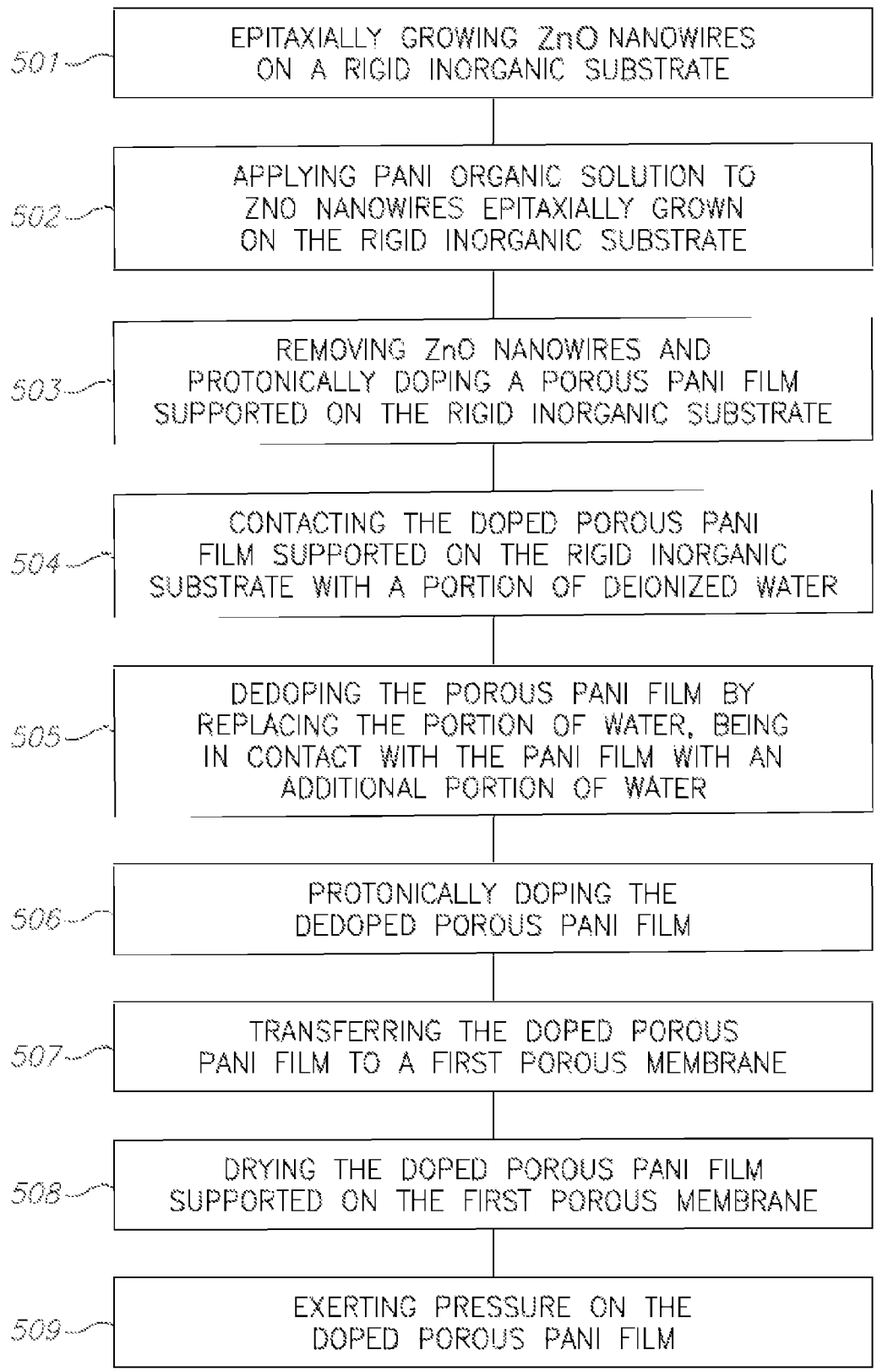
FIG. 4A: A flow chart of the LOFO method for the preparation of a protonically doped PANI porous film, according to some embodiments of the invention.
Figure 4B:
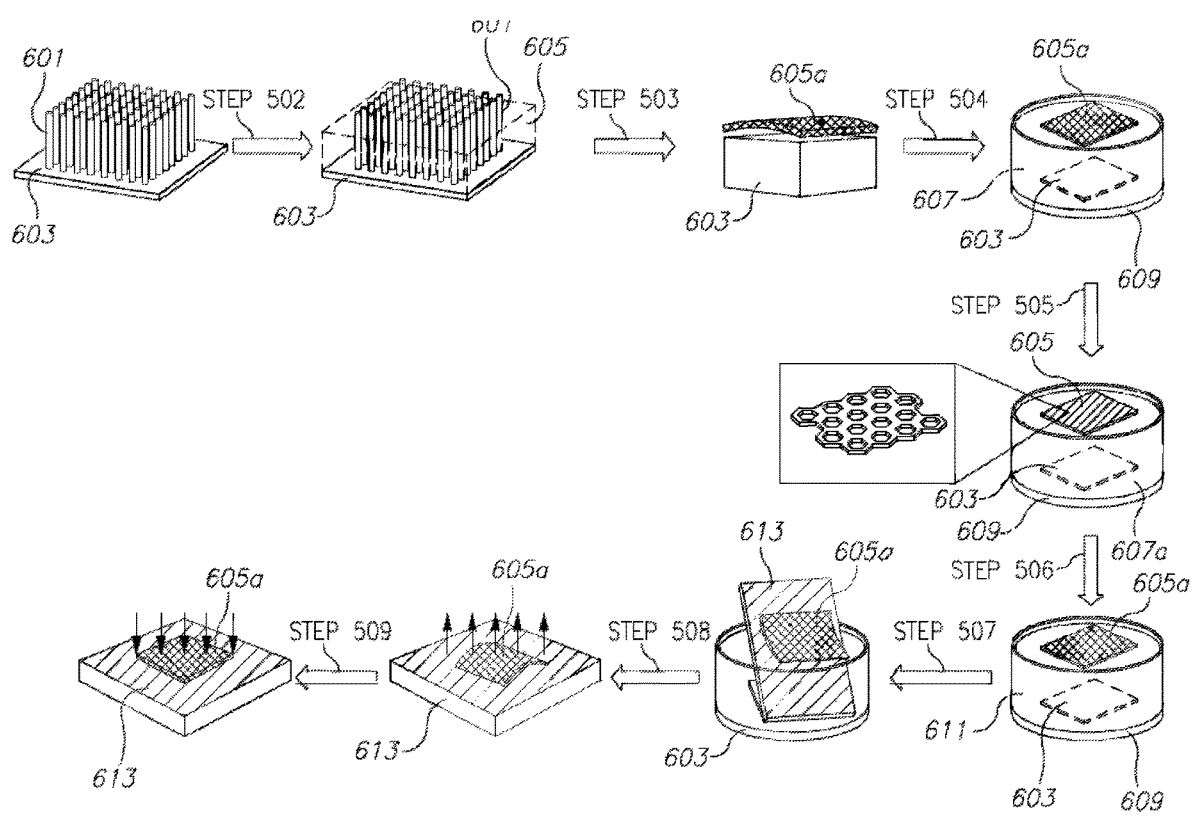
FIG. 4B: Schematic representation of the steps of the LOFO method presented in FIG. 4A.

According to some embodiments, the conducting polymer is PANI. In certain embodiments, the step of providing a conducting polymer porous film comprises the LOFO method adapted for providing a porous film. In certain such embodiments, the substrate is a substantially rigid inorganic substrate. The substrate can comprise ZnO nanowires. The rigid portion of the substrate can be made of glass. FIGS. 4A and 4B schematically represent the LOFO method step of providing a conducting polymer porous film according to some embodiments of the invention.

STEP 501: Epitaxially growing ZnO nanowires 601 on rigid inorganic substrate 603.

The nanowires can be grown by chemical bath deposition assisted by a seeding step, as described hereinabove.

STEP 502: Applying PANI organic solution to ZnO nanowires 601 epitaxially grown on rigid inorganic substrate 603.

PANI organic solution can be applied to the rigid inorganic substrate by a method selected from spin-coating, dip-coating, drop-coating, and screen printing, as described hereinabove. In certain embodiments, the step of applying PANI organic solution to the rigid inorganic substrate comprises spin-coating. In some embodiments, the spin-coating is performed at a rotating speed ranging from 500 rpm to about 5000 rpm. In further embodiments, the spin-coating is performed for a time period ranging from about 30 seconds to about 20 minutes. PANI film 605 is formed between ZnO nanowires.

STEP 503: Removing ZnO nanowires 601 and protonically doping porous PANI film 605 supported on rigid inorganic substrate 603 to obtain doped porous PANI film 605a.

In certain embodiments, doping the PANI film and/or removing the ZnO nanowires comprises immersing the PANI film supported on the substrate into an acidic solution. Non-limiting examples of the acids, which can be used for proton doping include hydrochloric acid, sodium bisulfite, salicylic acid, maleic acid, fumaric acid, phosphoric acid and any combination thereof. The concentration of the acidic solution can range from about 0.005M to about 10M, such as, for example, from about 0.005M to about 1M, from about 0.01 M to about 0.1M, or from about 1M to about 10M. Each possibility represents a separate embodiment of the invention.

STEP 504: Contacting doped porous PANI film 605a supported on rigid inorganic substrate 603 with a portion of deionized water 607, thereby separating doped porous PANI 605a film from rigid inorganic substrate 603.

In certain such embodiments, said contacting comprises immersing the PANI porous film supported on the rigid inorganic substrate in water or placing the PANI porous film supported on the rigid inorganic substrate on the water surface. According to some embodiments, doped porous PANI film 605a is placed in water tank 609, filled with water 607, wherein doped PANI film 605a floats on the water surface.

STEP 505: Dedoping porous PANI film 605a by replacing portion of water 607, being in contact with the PANI film with an additional portion of water 607a to obtain dedoped PANI film 605.

According to some embodiments, the LOFO method includes replacing the portion of water for at least two times. According to further embodiments, the LOFO method includes replacing the portion of water for at least three times. In still further embodiments, the water is replaced for at least three times in 48 hours.

STEP 506: Protonically doping dedoped porous PANI film 605.

Protonically doping the PANI film can comprise contacting the PANI film with acidic solution. In certain such embodiments, said contacting comprises immersing the porous PANI film in acidic solution or placing the PANI film on the solution surface. In particular embodiments, said contacting comprises removing water 607 from water tank 609 and filling it with acidic solution 611. Non-limiting examples of the acids, which can be used for proton doping include hydrochloric acid, sodium bisulfite, salicylic acid, maleic acid, fumaric acid, benzoic acid, phosphoric acid and any combination thereof. The concentration of the acidic solution can range from about 0.005M to about 10M, such as, for example, from about 0.005M to about 1M, or from about 0.01 M to about 0.1M. Each possibility represents a separate embodiment of the invention.

STEP 507: Transferring doped porous PANI film 605a to first porous membrane 613.

In some embodiments, said transferring comprises immersing first porous membrane 613 into water tank 609 and contacting doped porous PANI film 605a. In some embodiments, the first porous membrane comprises an electrode array disposed thereon.

STEP 508: Drying doped porous PANI film 605a supported on first porous membrane 611.

In some embodiments, the drying step comprises placing the porous PANI film supported on the first porous membrane in a vacuum chamber at a pressure of below about 10000 Pa.

STEP 509: Exerting pressure on doped porous PANI film 605a for the attachment thereof to first porous membrane 611.

In some embodiments, the method comprises increasing the pressure in the vacuum chamber to about 1 Atm or higher.

Preparation of the Electrode Array

According to some embodiments, the step of forming an electrode array on the first porous membrane, on the second porous membrane and/or on the self-healing polymer film comprising conductive nanostructures comprises depositing a metal on said membrane or film. The non-limiting methods of metal deposition include e-beam evaporation, physical vapor deposition, sputter-deposition, drop-casting, field enhanced deposition, soft lithography, inkjet printing, and screen printing. In some exemplary embodiments, the step of forming an electrode array comprises e-beam evaporation. The metal can be selected from Au, Ti, Cu, Ag, Pd, Pt, Ni, Al, and combinations thereof.

In certain embodiments, the step of forming an electrode array on the first porous membrane, on the second porous membrane and/or on the self-healing polymer film comprises applying a shadow mask to the membrane or film during the metal deposition. The shadow mask can be fabricated by any suitable process as known in the art. For example, a silicon wafer can be used, wherein a photoresist pattern is applied to the wafer and the wafer is etched for removing the silicon which is not protected by the photoresist.

Preparation of the First Porous Membrane

According to some embodiments, the step of providing a first porous membrane comprises preparing a solution of a polymer powder. Non-limiting examples of the polymers suitable for the preparation of the first porous membrane include polyvinylidene difluoride, (PVDF), Poly(vinylidene fluoride-co-hexafluoropropylene) (PVDF-HFP), polystyrene (PS), Poly(styrene-butadiene-styrene) (SBS), Nylon and combinations thereof. The polymer powder can have a molecular weight in the range from about 100,000 to about 200,000 g/mole.

A typical preparation procedure is as follows: A polymer powder is dissolved in an organic solvent. Non-limiting examples of organic solvents include N,N-Dimethylformamide, acetone, N,N-Dimethylacetamide, formic acid, Dichloromethane, Tetrahydrofuran (THF), dimethylformamide (DMF) and combinations thereof. The weight percent of the polymer powder in the solution can range from about 10% (w/w) to about 40% (w/w). In some embodiments, the weight percent of the polymer powder in the solution ranges from about 15% (w/w) to about 30% (w/w) or from about 15% (w/w) to about 25% (w/w). Each possibility represents a separate embodiment of the invention.

The mixing of the polymer powder and the organic solvent can proceed at a temperature ranging from about 15° C. to about 100° C. In certain embodiments, the mixing is performed at the room temperature. In other embodiments, the mixing is performed at the temperature of about 50° C.-80° C. The mixing time can range from about 1 to about 10 hours.

According to some embodiments, the step of providing a first porous membrane comprises forming the obtained solution of a polymer powder into a porous film. Various methods for forming a porous film, as known in the art, can be used, including, inter alia, spin-coating, casting from emulsion, and electively wetted surfaces. In some currently preferred embodiments, the step of providing a first porous membrane comprises electrospinning the obtained solution.

Electrospinning is a fiber production method which uses electric force to draw charged threads of polymer solutions or polymer melts up to fiber diameters in the order of some hundred nanometers. The standard setup for electrospinning comprises a spinneret (typically a hypodermic syringe needle) connected to a high-voltage (5 to 50 kV) direct current power supply, a syringe pump, and a grounded collector. A polymer solution is loaded into the syringe and said liquid is extruded from the needle tip at a constant rate by a syringe pump. Alternatively, the droplet at the tip of the spinneret can be replenished by feeding from a header tank providing a constant feed pressure.

Accordingly, in some embodiments, electrospinning comprises using at least one spinneret connected to a power source and a collecting drum. In some embodiments, the at least one spinneret is further connected to a pump.

In some embodiments, the at least one spinneret comprises a nozzle having an inner diameter ranging from about 100 µm to about 900 µm. In further embodiments, the nozzle has an inner diameter ranging from about 200 µm to about 800 µm, from about 300 µm to about 700 µm, or from about 400 µm to about 600 µm. Each possibility represents a separate embodiment of the invention. In some embodiments, the at least one spinneret comprises a nozzle having an outer diameter ranging from about 300 µm to about 1200 µm. In further embodiments, the nozzle has an outer diameter ranging from about 400 µm to about 1100 µm, from about 500 µm to about 1000 µm, or from about 600 µm to about 900 µm. Each possibility represents a separate embodiment of the invention.

In some embodiments, electrospinning is performed by feeding the solution to the spinneret at a feeding rate ranging from about 0.1 ml/hour to about 15 ml/hour. In further embodiments, electrospinning is performed by feeding the solution to the spinneret at a feeding rate ranging from about 0.1 ml/hour to about 5 ml/hour. The solution can be supplied to the spinneret by the pump. In some embodiments, the voltage applied to the spinneret by the power source ranges from about 8 Volt to about 60 Volt. In further embodiments, the voltage applied to the spinneret by the power source ranges from about 15 Volt to about 50 Volt.

In some embodiments, the distance between the nozzle and the collecting drum ranges from about 5 cm to about 40 cm. In further embodiments, the distance between the nozzle and the collecting drum ranges from about 12 cm to about 40 cm.

Preparation of the Second Porous Membrane

The method according to the principles of the present invention can further comprise a step of forming a second porous membrane on the conducting polymer porous film. The second porous membrane can separate the VOCs sensor from the pressure and temperature sensor disposed on the second porous membrane. The second porous membrane can be formed by applying a solution of a polymer powder onto said film. Non-limiting examples of the polymers suitable for the preparation of the second porous membrane include polyvinylidene difluoride, (PVDF), Poly(vinylidene fluoride-co-hexafluoropropylene) (PVDF-HFP), polystyrene (PS), Nylon and combinations thereof. The polymer powder can have a molecular weight in the range from about 100,000 to about 200,000 g/mole.

In some embodiments, the polymer powder is dissolved in an organic solvent. Non-limiting examples of organic solvents include N,N-Dimethylformamide, acetone, N,N-Dimethylacetamide, formic acid, Dichloromethane, Tetrahydrofuran (THF), dimethylformamide (DMF), and combinations thereof. The weight percent of the polymer powder in the solution can range from about 10% (w/w) to about 40% (w/w). In some embodiments, the weight percent of the polymer powder in the solution ranges from about 15% (w/w) to about 30% (w/w) or from about 15% (w/w) to about 25% (w/w). Each possibility represents a separate embodiment of the invention.

The mixing of the polymer powder and the organic solvent can proceed at a temperature ranging from about 15° C. to about 100° C. In certain embodiments, the mixing is performed at the room temperature. In other embodiments, the mixing is performed at the temperature of about 50° C.-80° C. The mixing time can range from about 1 to about 10 hours.

According to some embodiments, the step of forming a second porous membrane comprises electrospinning the obtained solution. In some embodiments, electrospinning comprises using at least one spinneret connected to a power source and a collecting drum.

In some embodiments, the at least one spinneret comprises a nozzle as described hereinabove.

In some embodiments, electrospinning is performed by feeding the solution to the spinneret at a feeding rate ranging from about 0.1 ml/hour to about 15 ml/hour. In further embodiments, electrospinning is performed by feeding the solution to the spinneret at a feeding rate ranging from about 0.1 ml/hour to about 5 ml/hour.

In some embodiments, the voltage applied to the spinneret by the power source ranges from about 8 Volt to about 60 Volt. In further embodiments, the voltage applied to the spinneret by the power source ranges from about 15 Volt to about 50 Volt.

In some embodiments, the distance between the nozzle and the collecting drum ranges from about 5 cm to about 40 cm. In further embodiments, the distance between the nozzle and the collecting drum ranges from about 12 cm to about 40 cm.

Preparation of the Self-Healing Film

In some embodiments, the method of the present invention further comprises a step of forming a self-healing film comprising mixing a self-healing polymer and conductive nanostructures selected from metallic nanoparticles capped with an organic coating; carbon-based nanostructures; and combinations thereof.

Non-limiting examples of suitable self-healing polymers include poly(propylene-urethaneureaphenyl-disulfide), poly (urethane-carboxyphenyl-disulfide), and poly(2-hydroxypropyl methacrylate)/poly(ethyleneimine).

In certain embodiments, the self-healing polymer is poly (propylene-urethaneureaphenyl-disulfide). Poly(propylene-urethaneureaphenyl-disulfide) can be synthesized as reported in Tan-Phat, and Hossam Haick. "Self-Healing, Fully Functional, and Multiparametric Flexible Sensing Platform." Advanced Materials 28 (2016): 138-143, the content of which is herein incorporated by reference in its entirety.

According to some embodiments, the step of preparing poly(propylene-urethaneureaphenyl-disulfide) is a one-step process. In further embodiments, said one-step process involves mixing polymer precursors comprising polymeric chains, comprising diisocyanate terminated polyether and amine-terminated crosslinking bridge molecules. In further embodiments, the crosslinking bridge molecules contain aromatic disulfide moieties. In still further embodiments, the polyether is a polypropylene. In yet further embodiments, the diisocyanate terminated polyether comprises aromatic isocyanate end groups. A non-limiting example of such aromatic diisocyanate end group includes tolylene diisocyanate. According to particular embodiments, the step of preparing the self-healing polymer comprises mixing 4-aminophenyl disulfide with poly(propylene glycol), tolylene 2,4-diisocyanate terminated.

The mixing of the polymer precursors is performed in a suitable solvent. Non-limiting examples of suitable solvents include tetrahydrofuran (THF), isopropanol, n-propanol, methanol, chloroform and combinations thereof.

According to certain embodiments, the step of preparing poly(propylene-urethaneureaphenyl-disulfide) comprises degassing the mixture of the polymer precursors under vacuum for at least about 10 minutes, preferably 15 minutes. According to some embodiments, the step of preparing poly(propylene-urethaneureaphenyl-disulfide) comprises curing of the obtained mixture for at least about 36 hours at the temperature of about 75° C. to about 85° C. In certain embodiments, the curing time is 48 hours and the curing temperature is 75° C.

In certain embodiments, the self-healing polymer is poly(urethane-carboxyphenyl-disulfide). Poly(urethane-carboxyphenyl-disulfide) can be synthesized as reported in Huynh Tan-Phat, Khatib M., Srour R., Plotkin M., Wu W., Vishinkin R., Hayek N., Jin H., Gazit O. M., Haick H. (2016). Composites of Polymer and Carbon Nanostructures for Self-Healing Chemical Sensors. Adv. Mater. Technol., 1: 1600187, the content of which is herein incorporated by reference in its entirety.

In some embodiments, poly(urethane-carboxyphenyl-disulfide) is synthesized by mixing polyurethane diol and 2,2'-dithiobenzoic acid with dimethylformamide. The resulting mixture can be stirred for about 0.5 h to 30 h at 70° C.-110° C., wherein $H_2SO_4$ can be added during mixing. Extraction of the final product can be performed by chloroform.

In certain embodiments, the self-healing polymer is poly(2-hydroxypropyl methacrylate)/poly(ethyleneimine). Poly(2-hydroxypropyl methacrylate)/poly(ethyleneimine) can be synthesized as reported in W. Huang, K. Besar, Y. Zhang, S. Yang, G. Wiedman, Y. Liu, W. Guo, J. Song, K. Hemker, K. Hristova, I. J. Kymissis, H. E. Katz, Adv. Funct. Mater. 2015, 25, 3745, the content of which is herein incorporated by reference in its entirety.

The conductive nanostructures can be selected from metallic nanoparticles capped with an organic coating and carbon nanostructures. Carbon nanostructures can include carbon powder, carbon nanotubes or graphite and can be purchased commercially. Metallic nanoparticles capped with an organic coating can be synthesized as is known in the art, for example using the two-phase method (Brust et al., J. Chem. Soc. Chem. Commun., 1994, 7, 801). In some embodiments, the method is modified (Hostetler et al., Langmuir 1998, 14, 17). In a non-limiting example, $AuCl_4^-$ is transferred from aqueous $HAuCl_4 \cdot xH_2O$ solution to a toluene solution by the phase-transfer reagent TOAB. After isolating the organic phase, excess thiols are added to the solution. The mole ratio of thiol: $HAuCl_4xH_2O$ can vary between 1:1 and 10:1, depending on the thiol used. This is performed in order to prepare mono-disperse solution of gold nanoparticles in an average size of about 3-6 nm. Exemplary procedures include, but are not limited to thiol: Au mole ratios of 10:1 and 1:1 for dodecanethiol and butanethiol-capped gold nanoparticles, respectively at an average size of about 5 nm. After vigorous stirring of the solution, aqueous solution of the reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene.

According to some embodiments, the step of mixing the self-healing polymer and conductive nanostructures comprises dispersing the conductive nanostructures in a solvent under sonication followed by the addition of the self-healing polymer and sonication.

In further embodiments, the method of the present invention comprises a step of applying the mixture of the self-healing polymer and conductive nanostructures onto the second porous membrane, thereby forming a pressure and temperature sensor. In certain embodiments, said step comprises electrospinning the mixture of the self-healing polymer and conductive nanostructures. In some embodiments, electrospinning comprises using at least one spinneret connected to a power source, and a collecting drum. In some embodiments, the at least one spinneret comprises a nozzle as described hereinabove. In some embodiments, electrospinning is performed by feeding the solution to the spinneret at a feeding rate ranging from about 0.1 ml/hour to about 5 ml/hour. In some embodiments, the voltage applied to the spinneret by the power source ranges from about 15 Volt to about 50 Volt. In some embodiments, the distance between the nozzle and the collecting drum ranges from about 12 cm to about 40 cm.

Preparation of the Third Porous Membrane

In further embodiments, the method according to the principles of the present invention comprises forming a third porous membrane. In some embodiments, the third porous membrane substantially covers the pressure and temperature sensor. The third membrane can be formed by applying a solution of a polymer powder onto the self-healing film. Non-limiting examples of the polymers suitable for the preparation of the third porous membrane include polyvinylidene difluoride, (PVDF), Poly(vinylidene fluoride-co-hexafluoropropylene) (PVDF-HFP), polystyrene (PS), Nylon and combinations thereof. The polymer powder can have a molecular weight in the range from about 100,000 to about 200,000 g/mole.

In some embodiments, the polymer powder is dissolved in an organic solvent. Non-limiting examples of organic solvents include N, N-Dimethylformamide, acetone, N, N-Dimethylacetamide, formic acid, Dichloromethane, Tetrahydrofuran (THF), dimethylformamide (DMF), and combinations thereof. The weight percent of the polymer powder in the solution can range from about 10% (w/w) to about 40% (w/w). In some embodiments, the weight percent of the polymer powder in the solution ranges from about 15% (w/w) to about 30% (w/w) or from about 15% (w/w) to about 25% (w/w). Each possibility represents a separate embodiment of the invention.

The mixing of the polymer powder and the organic solvent can proceed at a temperature ranging from about 15° C. to about 100° C. In certain embodiments, the mixing is performed at the room temperature. In other embodiments, the mixing is performed at the temperature of about 50° C.-80° C. The mixing time can range from about 1 to about 10 hours.

According to some embodiments, the step of forming a third porous membrane comprises electrospinning the obtained solution. In some embodiments, electrospinning comprises using at least one spinneret connected to a power source and a collecting drum.

In some embodiments, the at least one spinneret comprises a nozzle as described hereinabove.

In some embodiments, electrospinning is performed by feeding the solution to the spinneret at a feeding rate ranging from about 0.1 ml/hour to about 15 ml/hour. In further embodiments, electrospinning is performed by feeding the solution to the spinneret at a feeding rate ranging from about 0.1 ml/hour to about 5 ml/hour.

In some embodiments, the voltage applied to the spinneret by the power source ranges from about 8 Volt to about 60 Volt. In further embodiments, the voltage applied to the spinneret by the power source ranges from about 15 Volt to about 50 Volt.

In some embodiments, the distance between the nozzle and the collecting drum ranges from about 5 cm to about 40 cm. In further embodiments, the distance between the nozzle and the collecting drum ranges from about 12 cm to about 40 cm.

In certain embodiments, each one of the first porous membrane, second porous membrane, pressure and temperature sensor, and third porous membrane are formed by electrospinning. In some embodiments, the electrospinning process comprises electrospinning the first porous membrane polymer powder solutions on the collecting drum, forming the VOCs sensor on the first porous membrane, and sequentially electrospinning the respective polymer powder solutions and/or the mixture of the self-healing polymer and conductive nanostructures onto the platform unit.

In some embodiments, the process of the invention comprises evaporating the residue solvent from the platform unit. In certain embodiments, the process comprises placing the platform unit in a vacuum chamber. In further embodiments, the platform unit is placed into the vacuum chamber for at least about 24 hours.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" is generally employed in its sense including "and/or" unless the content clearly dictates otherwise.

As used herein, the term "about", when referring to a measurable value such as an amount, a temporal duration, and the like, is meant to encompass variations of +/−10%, more preferably +/−5%, even more preferably +/−1%, and still more preferably +/−0.1% from the specified value, as such variations are appropriate to perform the disclosed methods.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Preparation of the Porous Membranes

The first porous membrane, the second porous membrane and the third porous membrane were prepared as follows:

PVDF powder (Molecular weight=180000) was dissolved in N,N-Dimethylformamide and acetone, (v/v ratio from 1 to 0.3) or N,N-Dimethylacetamide and acetone (v/v ratio from 1 to 0.3) in a flask with weight concentration of 15-25% and reflux at 50-80 centigrade for 1-3 hour to get a transparent solution.

PVDF-HFP powder (Molecular weight=180000) was dissolved in THF/DMF or acetone/DMF solvent to form a homogeneous solution. The wt % of polymer was about 15%-20%, the ratio of THF/DMF or acetone/DMF ranged from 1/9 to 9/1.

PS powder (Molecular weight=140000) was dissolved in N,N-Dimethylformamide or N,N-Dimethylacetamide with weight concentration of 15-30% in a flask under stirring at room temperature for 1-10 hours to get a transparent solution.

Nylon (commercial powder) was dissolved in formic acid and Dichloromethane (v/v ratio from 0.8 to 0.2) with weight concentration of 15-30% in a flask under stirring at room temperature for 1-10 hours to get a transparent solution.

The obtained polymer powder solutions were electrospun to obtain a porous membrane. PVDF, PVDF-HFP, PS or Nylon solutions were put into a syringe with a metal nozzle of 7-20 outer diameter. The feeding rate was controlled from 0.1 ml/hour to 5 ml/hour for each syringe. A positive high voltage (15-50 V) was applied to the syringe and the distance between nozzle and collecting rotation drum was from 12 to 40 cm.

Figure 5A:
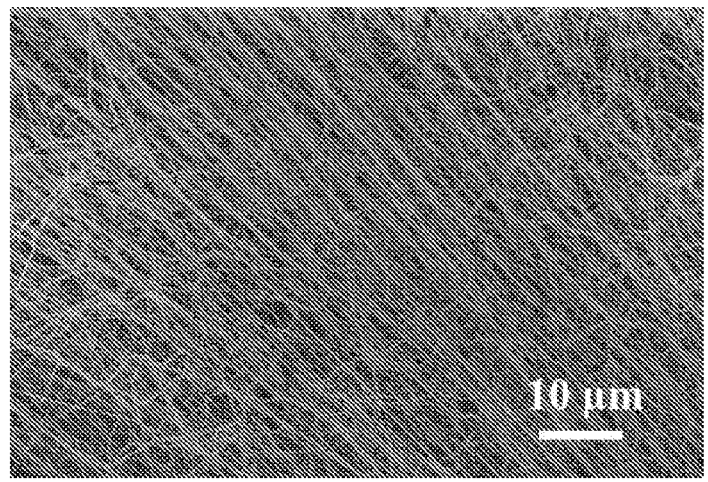
FIGS. 5A-5C: Scanning electron microscope (SEM) images of the first porous membrane, wherein the membrane is made of PVDF (FIG. 5A), PS (FIG. 5B), and Nylon (FIG. 5C).
Figure 5B:
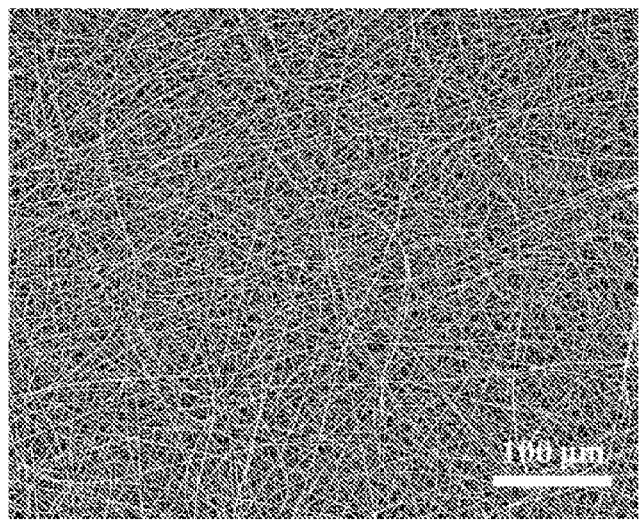
Figure 5C:
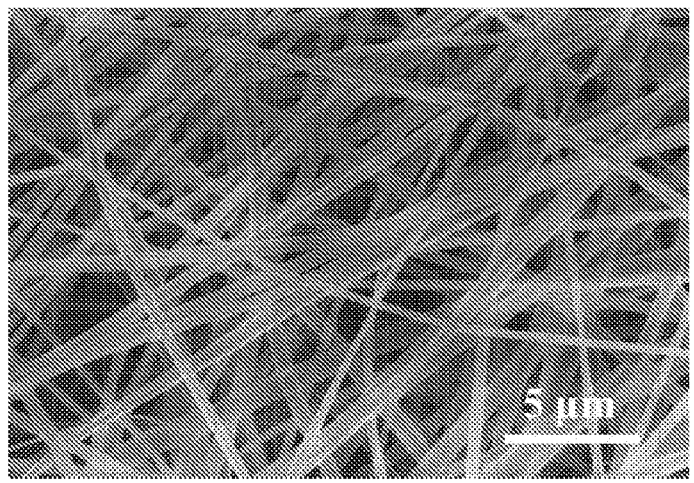
Figure 5D:
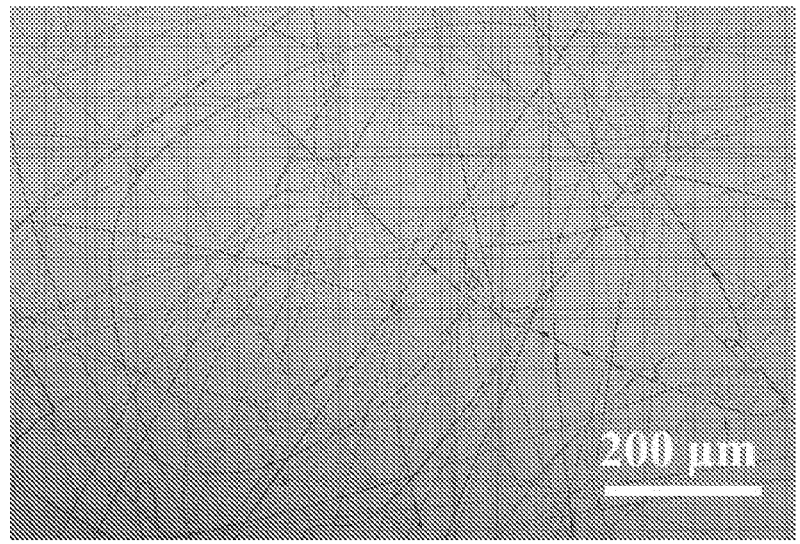
FIG. 5D: A photograph of the first porous membrane, wherein the membrane is made of PVDF-HFP.

Scanning electron microscope (SEM) micrographs of the PVDF, PS and Nylon electrospun porous membranes are shown in FIGS. 5A-5C, respectively. A photograph of PVDF-HFP electrospun porous membrane is shown in FIG. 5D. It can be clearly seen that the membranes comprise nanofibers and are porous, thereby allowing vapor permeability.

Example 2

Preparation of the Electrode Array

Figure 6:
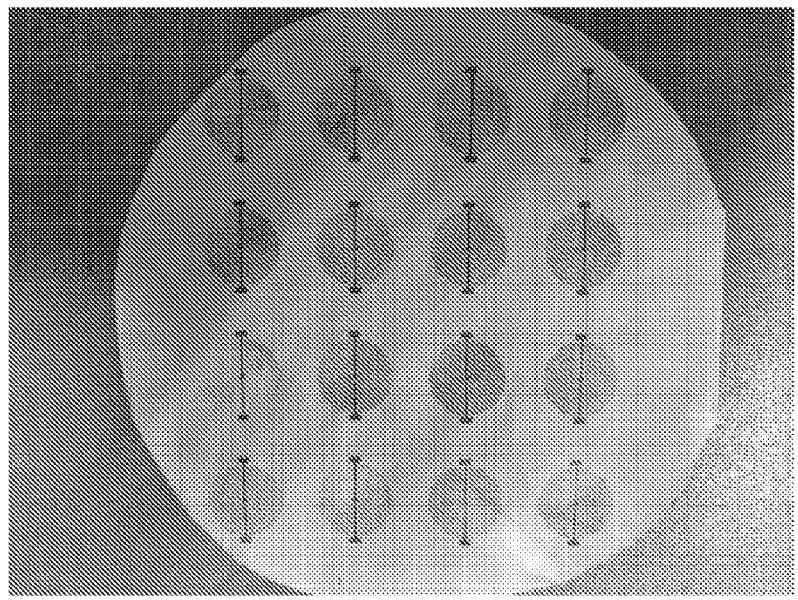
FIG. 6: A photograph of the first porous membrane made of PVDF-HFP, loaded with Au electrodes.

FIG. 6 is a photograph of the first porous membrane covered with electrode array. The gold electrodes were deposited onto the membrane using e-beam evaporation under the protection of shadow mask. The gold source was heated by electron beam. The rate of deposition was 1-5 A/s and electrode thickness was 50-200 nm.

Example 3

Preparation of the Conducting Polymer Porous Film

The schematic process of the preparation of the conducting polymer porous film is shown in FIGS. 4A and 4B. First, a seed layer of ZnO nanoparticles was deposited on a glass substrate using magnetron sputtering or drop casting. For magnetron sputtering commercial ZnO target can be used. The sputtering power was from 50 Watt to 1000 Watt under Ar atmosphere in a radio frequency sputtering model. When drop-casting method was used, ZnO nanoparticles were synthesized first, using solvent thermal method. Then, the ZnO nanoparticles were drop cast onto substrate and the substrate was baked at 250 to 350 centigrade. Then, an aqueous solution of $Zn(NO_3)_2$ (2 mM-25 mM) stabilized with Hexamethylenetetramine (HMTA) was used to grow ZnO nanowires array. The solution was kept at 60-100 centigrade and the growth process lasted 2-10 hours. Further details on the preparation of the ZnO nanowires can be found in Wu, Weiwei, et al. "Surface Engineering Method to Fabricate a Bendable Self-Cleaning Surface with High Robustness." *Science of Advanced Materials* 5.8 (2013): 933-938, which is incorporated herein by reference in its entirety.

Figure 7:
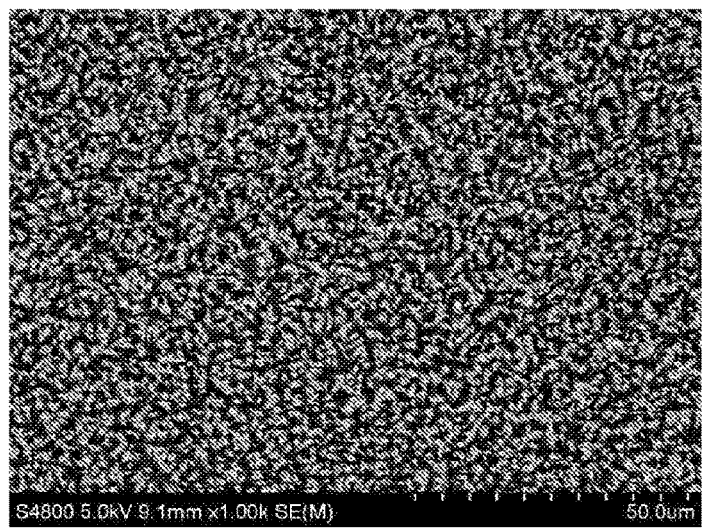
FIG. 7: Top view SEM image of ZnO nanowires array.

FIG. 7 shows a top view SEM image of ZnO nanowires array.

Following the preparation of the sacrificial template (ZnO nanowires array), a porous PANI film was prepared, as further presented in FIGS. 4A and 4B.

22.8 ml aniline, 25 ml hydrochloric acid and 250 ml DI water were mixed by overhead mechanical stirring in ice bath to form solution A. 28.505 g ammonium persulfate were dissolved in 250 ml DI water in ice bath to form solution B. Then solutions A and B were cooled down to 0° C. and solution B was added dropwise to solution A under stirring at a feeding rate of 250 ml/h. The reaction lasted for 8 hours at 0° C. The prepared doped PANI powder was rigorously washed with DI water and then immersed into pure ammonia for 12 hours. After filtration and washing using 5 L DI water, the PANI powder was soxhlet extracted by toluene, mixture of ethanol and water (v/v=9:1) in sequence to remove oligomer and salt for 72 h under the protection of $N_2$. After vacuum baking at 50° C. overnight, PANI powder was obtained. The powder was ground in an agate mortar manually.

PANI powder was dissolved in NMP with the concentration of 0.01 g/ml-0.1 g/ml. The solution was spin coated on ZnO nanowires array at rotating speed of 500 rpm-5000 rpm for 1-20 mins. Then, the glass substrate with the ZnO nanowires and coated PANI film was immersed into HCl solution (0.01 M-10 M) to remove ZnO nanowires array. Then, using the LOFO method according to the principles of the invention, the PANI film was left to float on DI water surface. DI water was changed many times in order to allow complete deprotonation of the PANI film. Then, solution containing dopants was used to dope the PANI film again. At last, the porous PANI film was transferred onto the first porous membrane comprising an electrode array. After drying, the VOCs sensor supported on the first porous membrane was obtained.

Figure 8A:
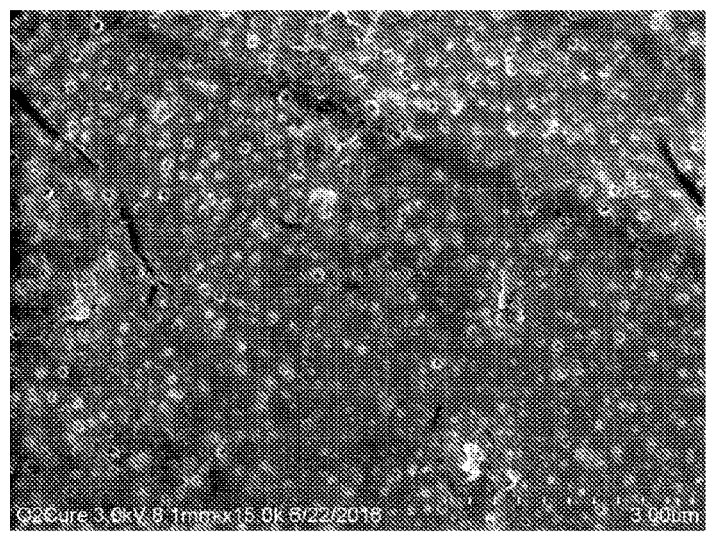
FIG. 8A: Top view SEM image of porous PANI film.
Figure 8B:
FIG. 8B: Cross sectional view SEM image of porous PANI film.

FIG. 8A shows a top view SEM image of the porous PANI film and FIG. 8B shows a cross sectional view SEM image of the porous PANI film. It can be clearly seen that the PANI film is porous, thereby allowing vapor permeability.

Figure 9:
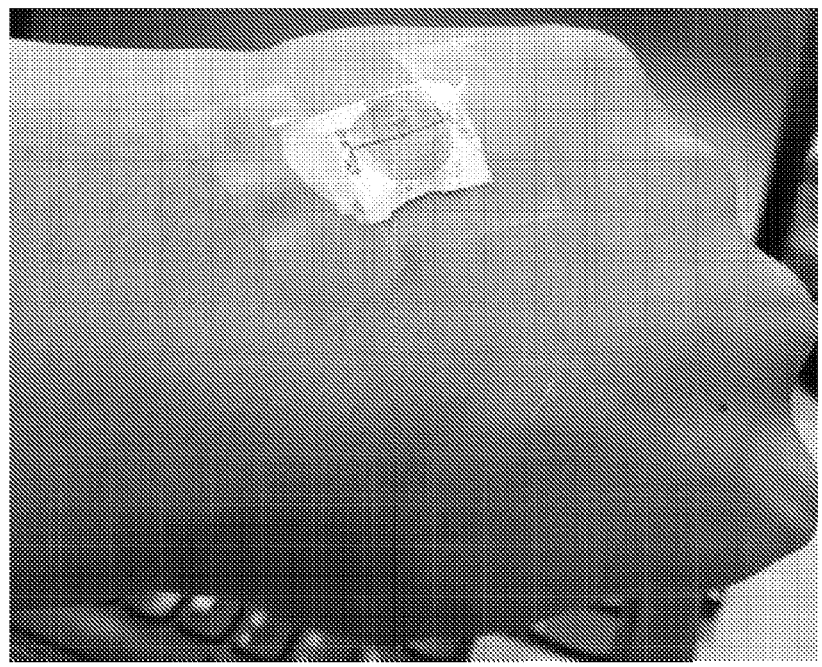
FIG. 9: Photograph of the VOCs sensor supported on the first porous membrane, which is attached to human skin.

FIG. 9 shows a photograph of the VOCs sensor supported on the first porous membrane, which is attached to human skin.

Example 4

Preparation of the Pressure and Temperature Sensor

Synthesis of the Self-Healing Polymer

Poly(propylene-urethaneureaphenyl-disulfide was synthesized as reported in Tan-Phat, and Hossam Haick. "Self-Healing, Fully Functional, and Multiparametric Flexible Sensing Platform." Advanced Materials 28 (2016): 138-143. Briefly, 4-Aminophenyl disulfide (750 mg, 3.0 mmole) was dissolved in 1 mL of tetrahydrofuran (THF) in a 100-mL beaker under ultrasonic condition. Then, poly(propylene glycol), tolylene 2,4-diisocyanate terminated, $M_w$=2300 (5.1 g, 2.2 mmole) was added and successively stirred for 15 min. Then, the obtained viscous mixture was transferred to a Teflon mold and degassed under vacuum for 15 min in order to completely remove the bubbles. Finally, the degassed viscous liquid was cured for 48 h at 75° C. The obtained product was a yellowish transparent elastomer.

Poly(urethane-carboxyphenyl-disulfide) was synthesized as reported in Huynh Tan-Phat, Khatib M., Srour R., Plotkin M., Wu W., Vishinkin R., Hayek N., Jin H., Gazit O. M., Haick H. (2016). Composites of Polymer and Carbon Nanostructures for Self-Healing Chemical Sensors. Adv. Mater. Technol., 1: 1600187. Briefly, 5 g polyurethane diol (Mw=320) and 500 mg 2,2'-dithiobenzoic acid were mixed with dimethylformamide (DMF; 3 mL), the resulting mixture being stirred for 1 h at 90° C. Concentrated $H_2SO_4$ (0.5 mL) was added and the solution stirred for a further 24 h at 90° C. The mixture was cooled to room temperature, and excess chloroform was added extract all the desired product. Following this, excess acid of the mixture was washed out with water. The dark-orange organic liquid layer collected was dried with anhydrous $Na_2SO_4$. After solvent evaporation, the organic layer compound was purified by liquid chromatography on a silica gel column using the chloroform:methanol (9:1, v:v) as the eluent (yield 1.53 g; 57%).

Poly(2-hydroxypropyl methacrylate)/poly(ethyleneimine) was synthesized as reported in W. Huang, K. Besar, Y. Zhang, S. Yang, G. Wiedman, Y. Liu, W. Guo, J. Song, K. Hemker, K. Hristova, I. J. Kymissis, H. E. Katz, Adv. Funct. Mater. 2015, 25, 3745.

Figure 10:
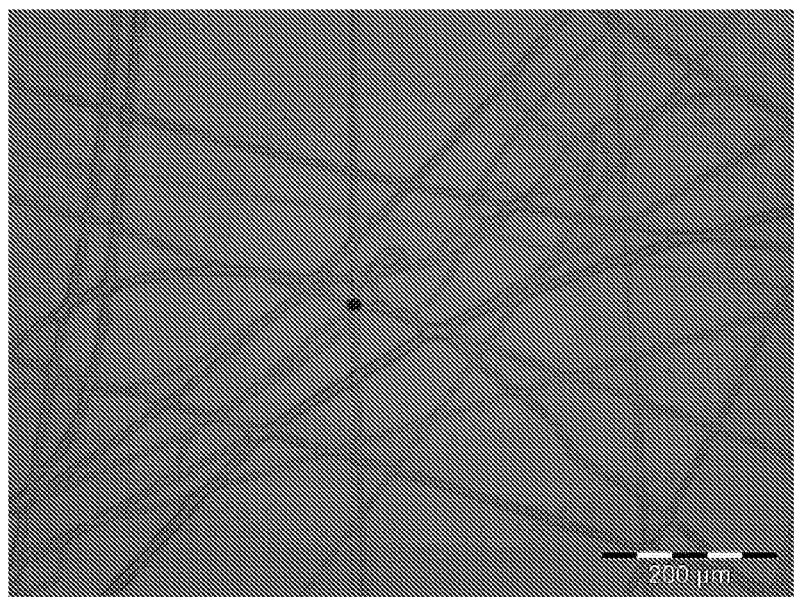
FIG. 10: magnified photograph of electrospun self-healing polymer membrane.

FIG. 10 shows a magnified photograph of electrospun poly(propylene-urethaneureaphenyl-disulfide self-healing film.

Synthesis of Metallic Nanoparticles

Metallic nanoparticles capped with an organic coating were synthesized using the two-phase method (Brust et al., J. Chem. Soc. Chem. Commun., 1994, 7, 801). Briefly, solution of $HAuCl_4$ was added to a stirred solution of TOAB in toluene. After 10 min stirring, the lower aqueous phase was removed. Organic ligands and sodium borohydride were subsequently added to the toluene phase. After 3 hours at ice temperature, the lower aqueous phase was removed and the toluene phase was subsequently evaporated by rotary evaporation. After first washing with cold ethanol, the solution was kept at 5° C. for 18 hours until complete immersion was achieved. The dark brown precipitate was filtered off and washed with ethanol.

Mixing of the Self-Healing Polymer and Conductive Nanostructures:

The self-healing polymer and the metallic nanoparticles were mixed as follows: gold nanoparticles (0.8 g) were dispersed in 0.35 ml toluene, then 0.2 g self-healing polymer was added and dissolved.

The self-healing polymer and the carbon nanostructures (including carbon powder, graphite and carbon nanotubes) were mixed as reported in Huynh Tan-Phat, Khatib M., Srour R., Plotkin M., Wu W., Vishinkin R., Hayek N., Jin H., Gazit O. M., Haick H. (2016). Composites of Polymer and Carbon Nanostructures for Self-Healing Chemical Sensors. Adv. Mater. Technol., 1: 1600187.

The mixtures of the self-healing polymer and conductive nanostructures were formed into a film by electrospinning. The feeding rate was 0.1 ml/h, the inner diameter of the nozzle was 0.5 mm, the voltage was 10 KV, the distance between the nozzle and collector drum was 8 cm.

Example 5

Fabrication of the Platform Unit

Following the preparation of the VOCs sensor supported on the first porous membrane, the sensor was fixed on the electrospinning collector. Depending on the desired platform unit structure, polymer powder solutions and/or the mixtures of the self-healing polymer and conductive nanostructures were electrospun layer by layer on top of the VOCs sensor. Electrospinning process conditions and solution compositions were as described in Examples 1 and 4. For example, when fabricating a platform unit as shown in FIG. 2, a polymer powder solution was electrospun on top of the VOCs sensor to form the second porous membrane, a mixture of the self-healing polymer and conductive nanostructures was electrospun onto the second porous membrane to form the pressure and temperature sensor and an additional polymer powder solution was electrospun on top of the pressure and temperature sensor to form the third porous membrane. Following the fabrication of all the platform unit layers, the platform unit was placed into a vacuum chamber for more than 24 hours to evaporate all the residue solvent.

Example 6

LOFO Method for the Preparation of a Protonically Doped Polyaniline (PANI) Thin Film PANI powder was prepared as described in Example 3. Then, 0.2 g of PANI powder was dissolved in 14 ml NMP to form a blue solution. A coverslip (1.8 cm*1.8 cm) was treated by $O_2$ plasma cleaning ($O_2$—Ar=50%-50%) for 30 mins to remove the organic residues on the surface, and, also, change the wetting property of coverslip to water and NMP. The contact angles of water and NMP decreased from 62±1° and 39±1° to 5.74±0.02° and 12±0.5°, respectively. Accordingly, the coverslip has good water and NMP wettability after $O_2$ plasma treatment. Without wishing to being bound by theory or mechanism of action, it is contemplated that the good wettability to NMP on coverslip is a key factor for obtaining high quality PANI film by spin-coating. Then, PANI solution (25 μL) was dropped onto the coverslip and spincoated at 1000 rpm (6 mins), 3500 rpm (30 s) and 1000 rpm (4 mins) in sequence to form a uniform PANI thin film. At last, the coverslip covered with the PANI thin film was stored in a vacuum chamber overnight.

Figure 11A:
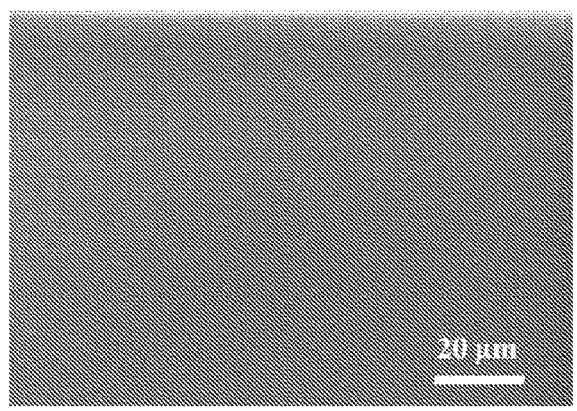
FIGS. 11A-11D: Top (FIG. 11A) and cross sectional (FIG. 11B) view SEM images of PANI film without dopant. Top (FIG. 11C) and cross-sectional (FIG. 11D) view SEM images of PANI film doped with hydrochloric acid.
Figure 11B:
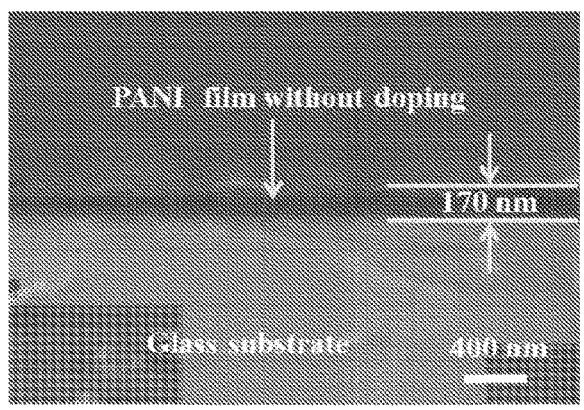

FIG. 11A is a top view SEM image of the PANI thin film. As can be seen from the image, the film is continuous and smooth without any microscale defects. The thickness of the film without a dopant is about 170 nm as shown in the cross sectional SEM image (FIG. 11B).

Figure 11C:
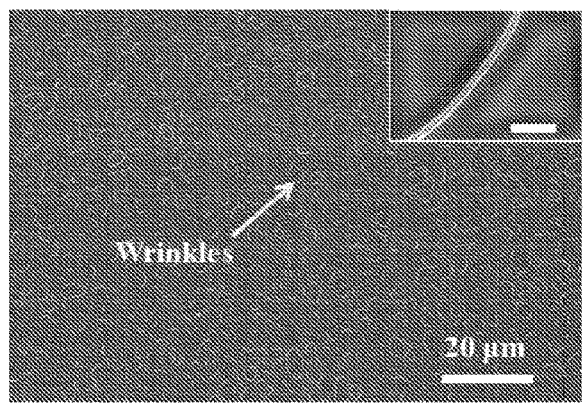
Figure 11D:
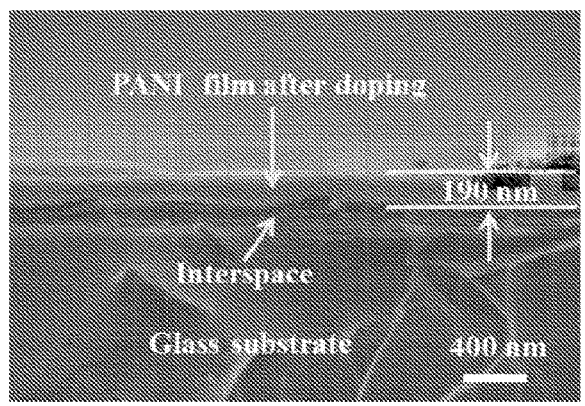

The obtained PANI film was treated by various dopants in a form of volatile acid vapor for a few seconds. The dopants included hydrochloric acid, sodium bisulfate, salicylic acid, maleic acid, fumaric acid, and phosphoric acid. After slightly doping with a volatile acid, the color of the film turned from blue to green, indicating the state of polyaniline change from pemigraniline base to emeraldine salt. As shown in FIG. 11C, the film swells and has a lot of wrinkles on the top surface. Those wrinkles are distributed throughout the film. The thickness of the doped PANI film changes to 190 nm, as shown in FIG. 11D. The volume expansion of the PANI film as a result of doping leads to an obvious interspace marked by a yellow arrow in FIG. 11D that plays an important role in the LOFO process of the present invention.

To transfer the PANI film from the rigid substrate to flexible substrate, the LOFO approach has been developed featuring slight volatile acid doping and water only transfer process, as schematically presented in FIGS. 3A and 3B. Under the effect of surface tension of water and low density of the PANI film, the doped PANI film floats on the surface of water, whilst the dedoping process happens due to the good solubility of dopant in water. The DI water was replaced at least 3 times during 48 hours for dedoping all the dopants. After that, pure PANI film on DI water surface was doped again though replacing DI water with dopant solution. The floating and doped film was transferred to different kinds of substrates. The substrates included flat, convex, concave and hollow shapes. After that, the PANI film supported on a substrate was placed into a vacuum chamber to evaporate the residue water. At last, the chamber was recovered to atmospheric pressure with clean air that pushed the film attachment to the substrate. Typically, the substrate was made of PET.

Figure 12A:
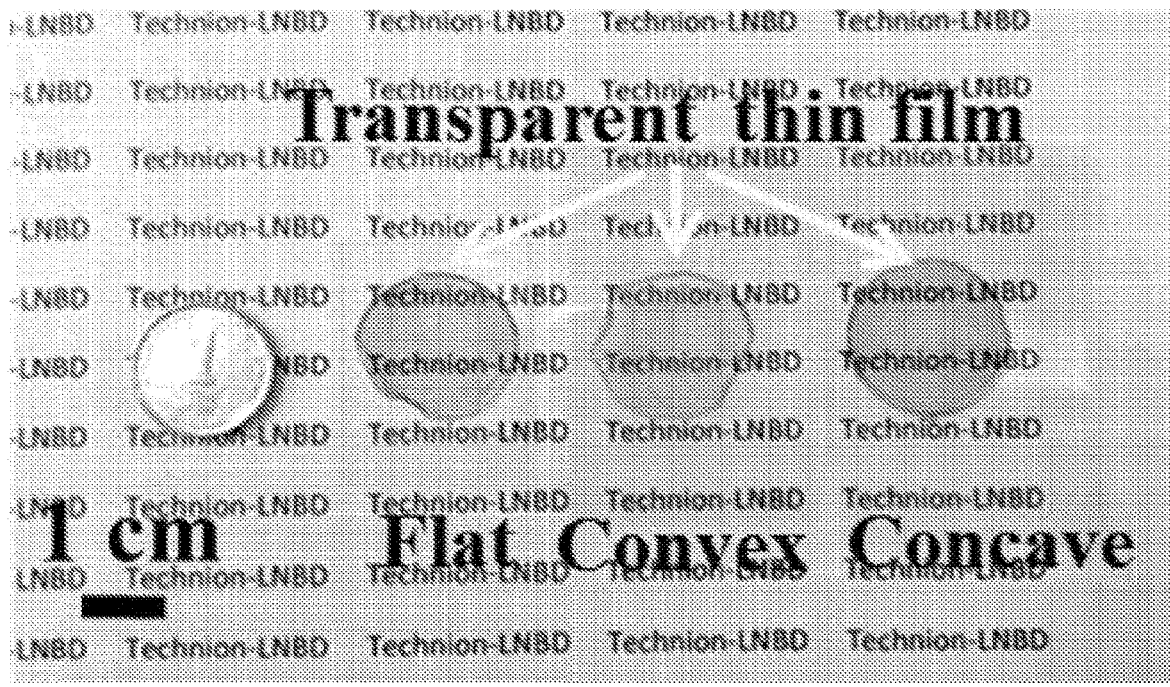
FIG. 12A: Photograph of flat, convex and concave polyethylene terephthalate (PET) substrates covered with doped PANI film.
Figure 12B:
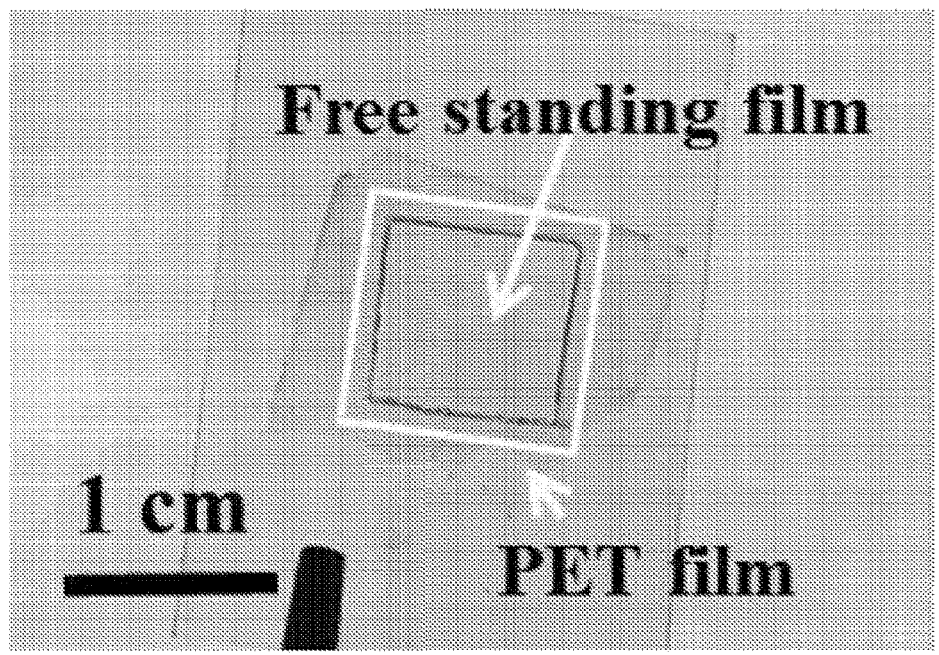
FIG. 12B: Photograph of the free-standing doped PANI film.
Figure 12C:
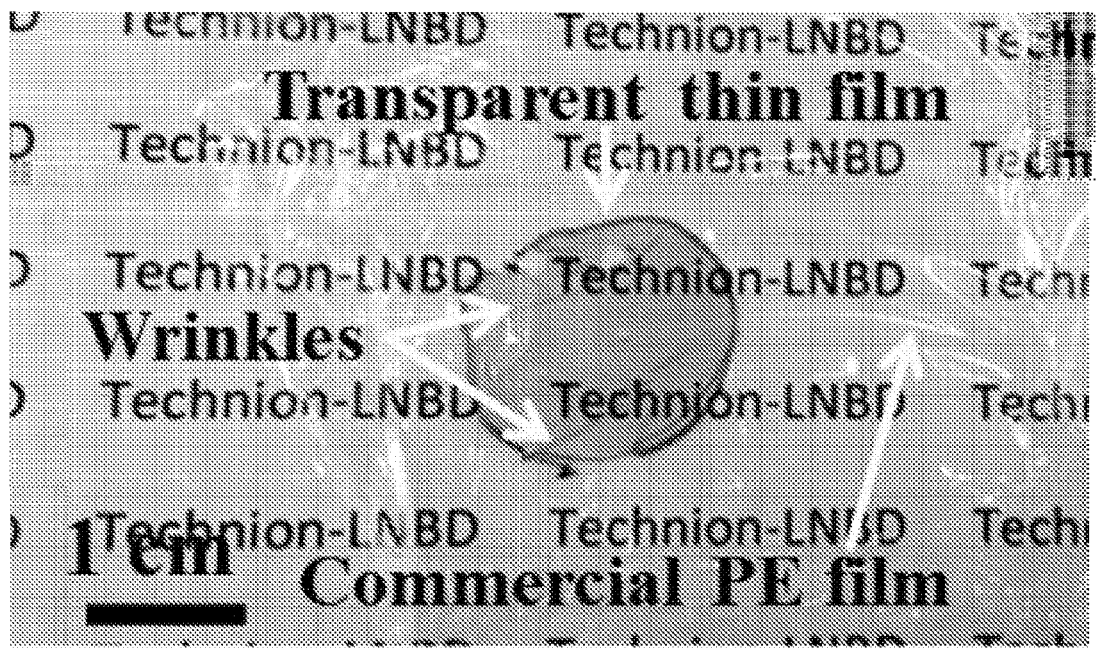
FIG. 12C: Photograph of the commercial PET substrate covered with doped PANI film.
Figure 12D:
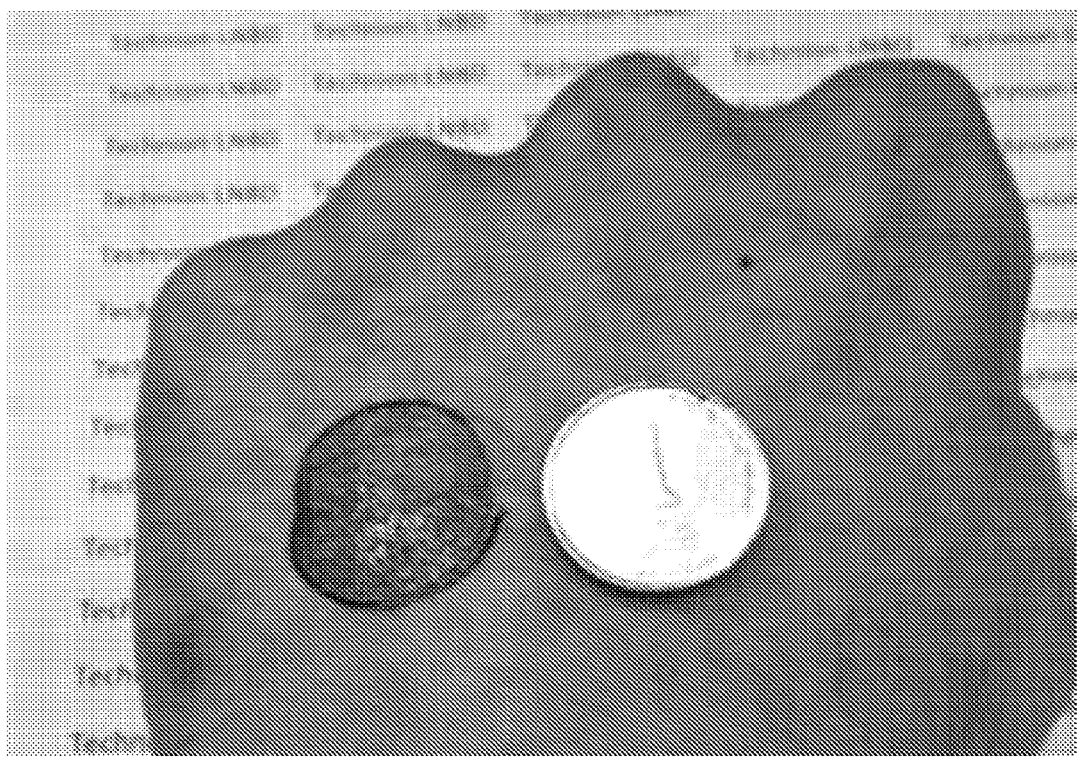
FIG. 12D: Photograph of the tattoo-like doped PANI film on human hand.
Figure 12E:
FIG. 12E: Photograph of the 4 inches-sized doped PANI film on PET substrate.

FIG. 12A shows representative photographs of doped PANI films transferred onto flat, convex and concave PET substrates. Freestanding PANI films were fabricated by transferring the doped PANI film on a hollow substrate (FIG. 12B) due to the good mechanical stability thereof. FIG. 12C is a photograph of the doped PANI film transferred onto a commercial PE film. The doped PANI film is tightly adhered to the PET film, replicating the wrinkles marked by yellow arrows. As shown in FIG. 12D, doped PANI film can adhere to the human skin as a tattoo. Furthermore, using the LOFO method of the invention, wafer scale doped PANI film (4 inches) can be transferred to PET substrate as shown in FIG. 12E, which is promising for practical application via industrial routes.

Example 7

Sensitivity of Doped PANI Film to Lateral Strain

PANI films doped with various dopants, including sodium bisulfate, salicylic acid, maleic acid, fumaric acid, and phosphoric acid were prepared by the LOFO method as described in Example 6. The doped PANI films were transferred to PET substrates covered with interdigitated electrodes, to obtain sensors including PANI films doped with said various dopants. The electrodes were made from gold, due to its high work function, which facilitates formation of ohmic contact between gold electrodes and p-type PANI in the metal-semiconductor interface. The ohmic contact means that the variation of resistance of the PANI-based sensor is due to the thin film rather than the interface barriers.

Figure 13:
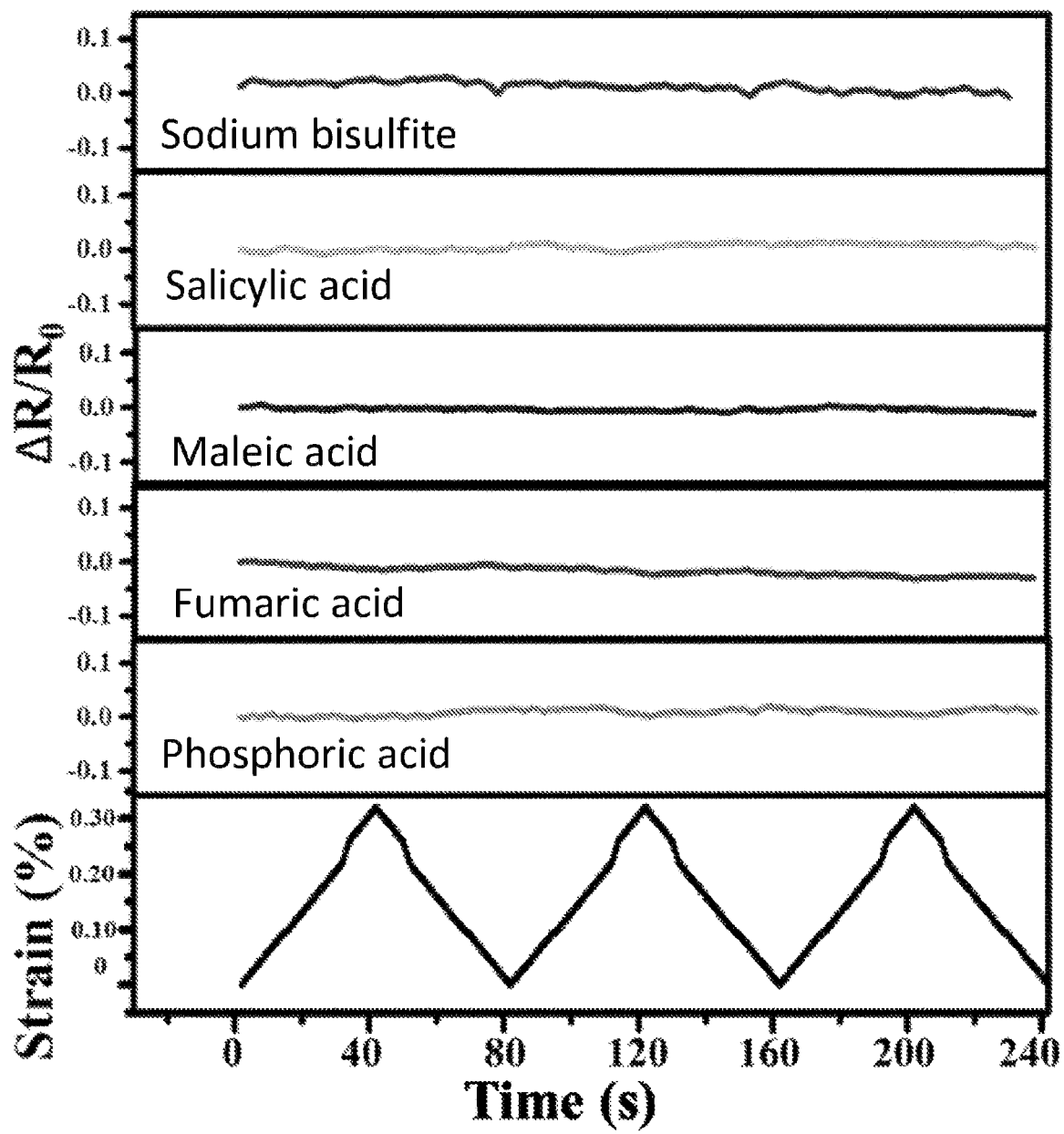
FIG. 13: Normalized relative resistance change and strain versus time curve of doped PANI film-based sensors supported on PET substrate, wherein PANI is doped with sodium bisulfate, salicylic acid, maleic acid, fumaric acid and phosphoric acid.

FIG. 13 presents the relative resistance ($R/R_0$; where R is the resistance under lateral strain and $R_0$ is the resistance without laterally strain) of the PANI-based sensor, when strain is repeatedly applied to the PET substrate and released by a bending machine. The thickness of the PET substrate was 250 μm. When the PET substrate was bent, the bottom surface was stretched and a lateral strain calculated as reported in (Yang, R., Qin, Y., Dai, L. & Wang, Z. L. Power generation with laterally packaged piezoelectric fine wires. *Nat Nano* 4, 34-39 (2009)) was applied to the PANI film. FIG. 13 indicates that all the $R/R_0$ values of the PANI film-based sensors, wherein PANI is doped with different dopants including sodium bisulfate, salicylic acid, maleic acid, fumaric acid, and phosphoric acid, are in the region of 1±0.02 when the strain (0-0.32%) is applied and released with a strain rate of ±0.008%/s periodically at a fixed pressure, temperature and atmospheric VOCs composition. Thus, the doped PANI film-based sensors were found to have stable resistances under lateral strain, thereby allowing their use in flexible devices.

Example 8

Sensitivity of Doped PANI Film to VOCs

Figure 14A:
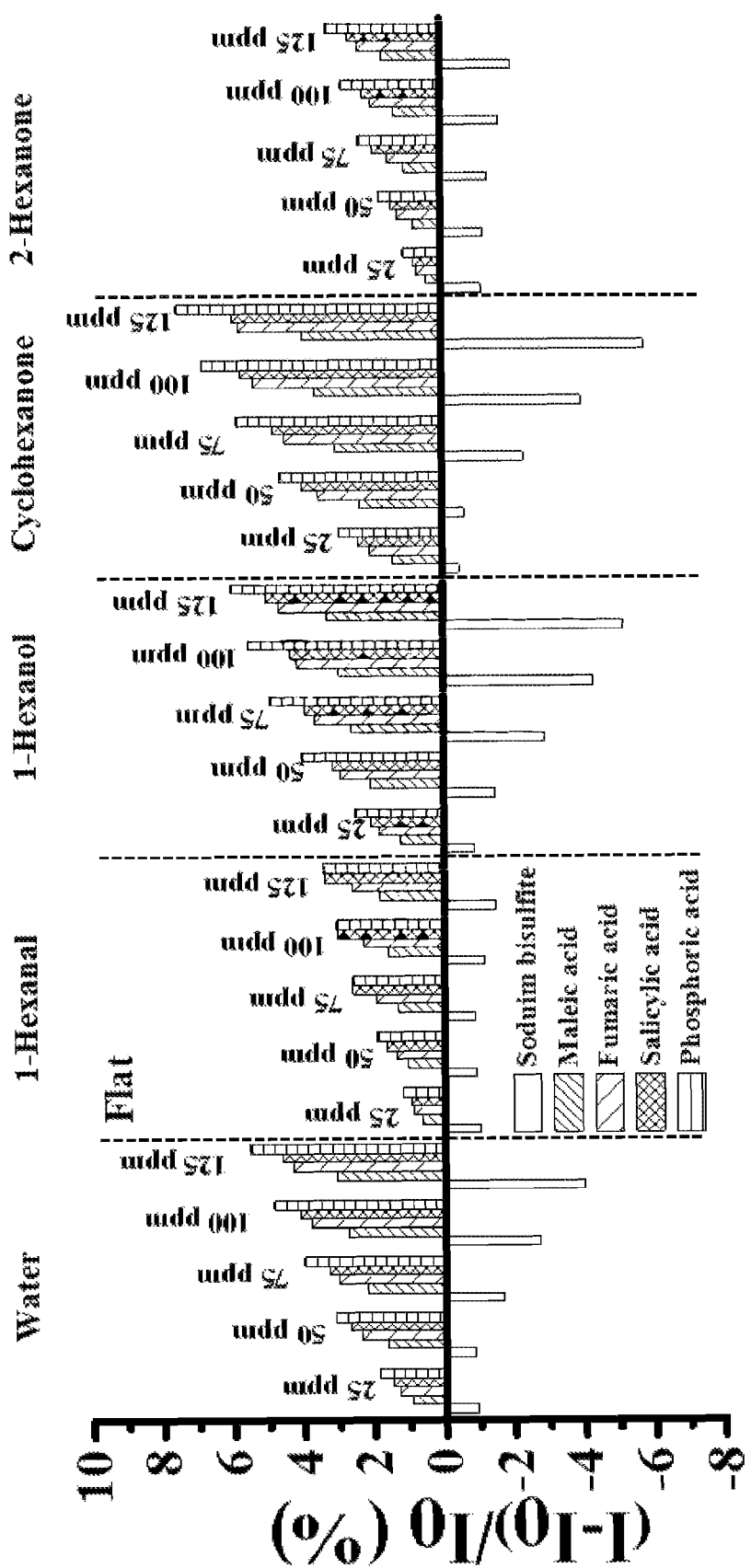
FIG. 14A: Bar diagrams of the response of the doped PANI-based sensors to different VOCs under flat state: from left to right the response of the sensors to water, 1-hexanal, 1-hexanol, cyclohexanone, and 2-hexanone. Solid bar represents sodium bisulfite dopant, upward diagonal bar represents maleic acid dopant, wide backward diagonal bar represents fumaric acid dopant, diagonal grid bar represents salicylic acid, and horizontal line bar represents phosphoric acid dopant.
Figure 14B:
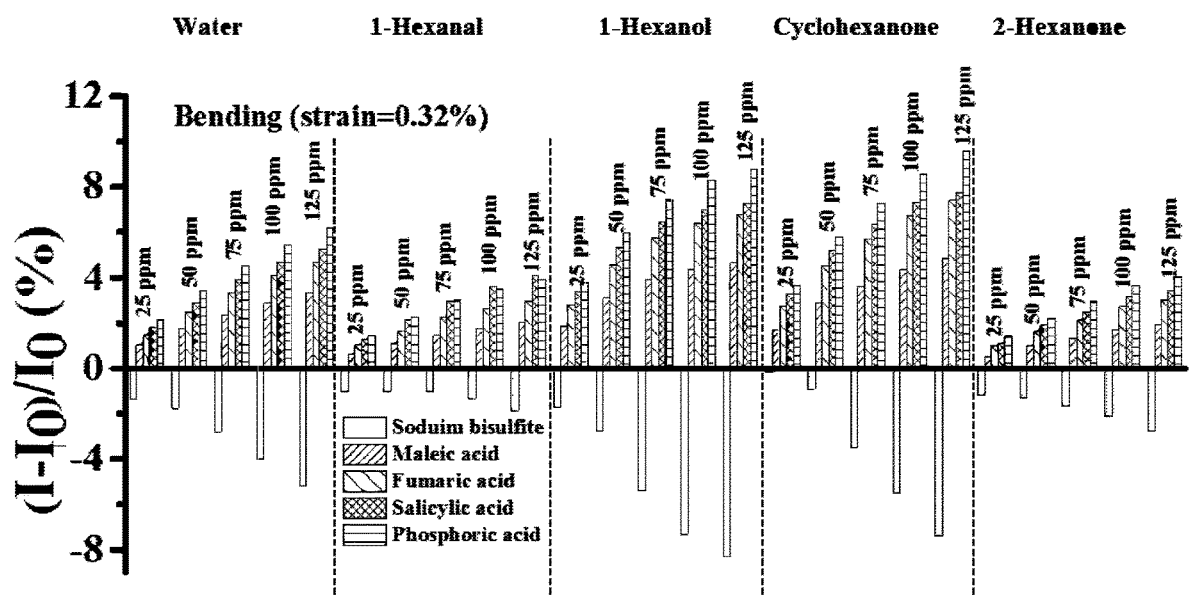
FIG. 14B: Bar diagram of the response of the doped PANI-based sensor to different VOCs under bending state: from left to right the response of the sensors to water, 1-hexanal, 1-hexanol, cyclohexanone, and 2-hexanone. Solid bar represents sodium bisulfite dopant, upward diagonal bar represents maleic acid dopant, wide backward diagonal bar represents fumaric acid dopant, diagonal grid bar represents salicylic acid, and horizontal line bar represents phosphoric acid dopant.

The utility of the doped PANI-based sensors as prepared in Example 6 for the detection and classification of VOCs were evaluated. Sensitivity of the sensors to water and VOCs having 6 carbon atoms but different polarities was examined under flat and bending states. The VOCs included 1-hexanal, 1-hexanol, cyclohexanone and 2-hexanone. These VOCs were chosen because they are highly correlative with the exhaled VOCs both from the respiratory tract and skin, which have been considered as biomarkers for disease diagnose and health monitoring. The pressure and temperature were kept at 760 Torr and 25° C. during the measurements, respectively. The concentration of VOCs analytes ranged from 25 ppm to 125 ppm with an increment of 25 ppm. FIGS. 14A and 14B show bar diagram of sensors' responses to different VOCs and water. It can be seen that the detection of VOCs by the doped PANI-based sensors is not only qualitative but also quantitative in both flat and bending state.

The change in resistance of the doped PANI-based sensors in response to various VOCs was lower than ten percent as shown in FIGS. 14A and 14B. The pressure changes caused responses lower than 2.5 percent and temperature sensing ranged from tens to hundreds percent level. Without wishing to being bound by theory or mechanism of action, it is contemplated that the response of flexible doped PANI-based sensors to VOCS, pressure and temperature can be decoupled due to the difference in the response amplitude of the sensors to said stimuli. Alternatively, the doped PANI-based sensor for the detection of VOCs can be coupled with a temperature and/or pressure sensor to calibrate the PANI-based sensor at any given temperature and/or pressure and to eliminate the effect thereof on the PANI-based VOCs sensor.

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

We claim:

1. A vapor-permeable flexible sensing platform unit comprising:
   a first porous membrane, wherein the first porous membrane is substantially flexible and hydrophobic; and
   a volatile organic compounds (VOCs) sensor disposed on the first porous membrane, the VOCs sensor comprising an electrode array and a conducting polymer porous film being in electric contact with said electrode array,
   wherein the VOCs sensor is insensitive to lateral strain such that an output signal of the VOCs sensor remains stable under lateral strain.

2. The platform unit according to claim 1, wherein the conducting polymer is selected from the group consisting of polyaniline (PANI), polypyrrole, polydiketopyrrolopyrrole, polythiophene, poly(3,4-ethylenedioxythiophene)-poly(styrene-sulfonate) (PEDOT:PSS).

3. The platform unit according to claim 2, wherein the conducting polymer is PANI, which is protonically doped with a dopant selected from the group consisting of hydrochloric acid, sodium bisulfite, salicylic acid, maleic acid, fumaric acid, benzoic acid, phosphoric acid and any combination thereof.

4. The platform unit according to claim 1, wherein the conducting polymer porous film has at least one non-uniform surface.

5. The platform unit according to claim 1, wherein the conducting polymer porous film has a vertically ordered porous structure.

6. The platform unit according to claim 5, wherein the conducting polymer porous film has a mean pore size ranging from about 20 nm to about 500 nm or a porosity ranging from about 30% to about 80% of the total film volume.

7. The platform unit according to claim 1, further comprising a pressure and temperature sensor, wherein said pressure and temperature sensor comprises a self-healing porous film, comprising a self-healing polymer and conductive nanostructures selected from the group consisting of metallic nanoparticles capped with an organic coating, carbon-based nanostructures and combinations thereof.

8. The platform unit according to claim 7, wherein said self-healing polymer is selected from the group consisting of poly(propylene-urethaneureaphenyl-disulfide), poly(urethane-carboxyphenyl-disulfide), and poly(2-hydroxypropyl methacrylate)/poly(ethyleneimine).

9. The platform unit according to claim 7,
   wherein the metallic nanoparticles are selected from the group consisting of Au, Ag, Ni, Co, Pt, Pd, Cu, Al, Zn, Fe, and combinations thereof or wherein the metallic nanoparticles comprise metal alloys selected from the group consisting of Au/Ag, Au/Cu, Au/Ag/Cu, Au/Pt, Au/Pd, Au/Ag/Cu/Pd, Pt/Rh, Ni/Co, and Pt/Ni/Fe, or
   wherein said carbon-based nanostructures are selected from the group consisting of carbon powder, carbon nanotubes, graphite and combinations thereof.

10. The platform unit according to claim 7, wherein the self-healing porous film comprises nanofibers.

11. The platform unit according to claim 7, wherein the self-healing porous film has a mean pore size ranging from about 100 nm to about 5 µm or a porosity ranging from about 30% to about 80% of the total film volume.

12. The platform unit according to claim 7, wherein the VOCs sensor, the pressure and temperature sensor, or both, are configured in a form of a resistive sensor.

13. The platform unit according to claim 7, further comprising:
   (i) a second porous membrane disposed between the VOCs sensor and the pressure and temperature sensor, wherein said second porous membrane is electrically insulating or
   (ii) a third porous membrane, substantially covering the pressure and temperature sensor,
   wherein the third porous membrane is hydrophobic and self-cleaning.

14. The platform unit according to claim 13, wherein at least one of the first porous membrane, the second porous membrane, or the third porous membrane comprise a polymer selected from the group consisting of polyvinylidene difluoride, (PVDF), Poly(vinylidene fluoride-co-hexafluoropropylene) (PVDF-HFP), polystyrene (PS), Poly(styrene-butadiene-styrene) (SBS), Nylon and combinations thereof.

15. The platform unit according to claim 13, wherein at least one of the first porous membrane, the second porous membrane, or the third porous membrane has a mean pore size ranging from about 20 nm to about 20 µm and/or a porosity ranging from about 30% to about 90% of the total membrane volume.

16. A method for fabricating the vapor-permeable flexible sensing platform unit according to claim 1, the method comprising:
   i. providing the first porous membrane which is substantially flexible and hydrophobic;
   ii. forming the electrode array;
   iii. providing the conducting polymer porous film; and iv. disposing said conducting polymer porous film on the electrode array or the first porous membrane, wherein the conducting polymer porous film is in electric contact with the electrode array, thereby forming the VOCs sensor.

17. The method according to claim 16,
wherein the step of providing the conducting polymer porous film comprises applying a solution of a conducting polymer onto a substrate having a non-uniform surface, and
wherein the step of providing the conducting polymer porous film is performed by a process selected from the group consisting of spin-coating, dip-coating, drop-coating, and screen printing.

18. The method according to claim 17, wherein said substrate comprises nanostructures epitaxially grown thereon, wherein the nanostructures are selected from the group consisting of nanowires, nanorods, nanotubes, nanoneedles and combinations thereof.

19. The method according to claim 18, wherein the conducting polymer is PANI, the substrate is a substantially rigid inorganic substrate comprising ZnO nanowires; and the step of providing a conducting polymer porous film further comprises protonically doping the PANI film.

20. The method according to claim 19, further comprising:
contacting the doped PANI film supported on the substrate with a portion of deionized water, thereby separating the doped PANI film from the substrate;
dedoping the PANI film by replacing the portion of water, being in contact with the PANI film with an additional portion of deionized water; and
protonically doping the dedoped PANI film,
wherein the protonical doping comprises contacting the PANI film with an acidic solution comprising an acid selected from the group consisting of hydrochloric acid, sodium bisulfite, salicylic acid, maleic acid, fumaric acid, benzoic acid, phosphoric acid and any combination thereof.

* * * * *